US006217525B1

(12) United States Patent
Medema et al.

(10) Patent No.: US 6,217,525 B1
(45) Date of Patent: *Apr. 17, 2001

(54) REDUCED LEAD SET DEVICE AND METHOD FOR DETECTING ACUTE CARDIAC ISCHEMIC CONDITIONS

(75) Inventors: Douglas K. Medema, Everett; Tae H. Joo, Redmond; Paul W. Schmitt; David R. Hampton, both of Woodinville; Robert A. Niskanen, Seattle, all of WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/229,977

(22) Filed: Jan. 13, 1999

Related U.S. Application Data

(63) Continuation-in-part of application No. 09/209,879, filed on Dec. 11, 1998.
(60) Provisional application No. 60/083,722, filed on Apr. 30, 1998, and provisional application No. 60/100,391, filed on Sep. 15, 1998.

(51) Int. Cl.[7] .................................................. A61B 5/0402
(52) U.S. Cl. .............................................. 600/508; 607/5
(58) Field of Search ............................ 607/4–6; 600/508, 600/509, 512, 515, 516

(56) References Cited

U.S. PATENT DOCUMENTS

| 3,631,851 | 1/1972 | Hesen . |
|---|---|---|
| 4,106,495 | 8/1978 | Kennedy . |
| 4,318,412 | 3/1982 | Stanly et al. . |
| 4,708,144 | 11/1987 | Hamilton et al. . |
| 4,802,491 | 2/1989 | Cohen et al. . |
| 4,850,370 | 7/1989 | Dower . |
| 4,883,064 | 11/1989 | Olson et al. . |
| 4,919,145 | 4/1990 | Marriott . |
| 4,924,875 | 5/1990 | Chamoun . |
| 4,940,054 | 7/1990 | Grevis et al. . |
| 4,974,598 | 12/1990 | John . |
| 5,010,888 | 4/1991 | Jadvar et al. . |
| 5,020,541 | 6/1991 | Marriott . |
| 5,042,498 | 8/1991 | Dukes . |
| 5,058,598 | 10/1991 | Nicklas et al. . |
| 5,159,932 | 11/1992 | Zanetti et al. . |
| 5,161,539 | 11/1992 | Evans et al. . |
| 5,181,519 | * 1/1993 | Bible ................................... 600/509 |

(List continued on next page.)

FOREIGN PATENT DOCUMENTS

| 0 467 695 A2 | 1/1992 | (EP) . |
|---|---|---|
| 0 711 531 A1 | 5/1996 | (EP) . |
| WO 96 24905 | 8/1996 | (WO) . |

*Primary Examiner*—George R. Evanisko
(74) *Attorney, Agent, or Firm*—Christensen O'Connor Johnson Kindness PLLC

(57) ABSTRACT

A reduced lead set device (10) that detects and reports the presence of an acute cardiac ischemic condition in a patient includes a reduced set of sensing electrodes (12, 14, 16, 18, and 20) placed on a patient for acquiring ECG data from the patient. The reduced lead set device evaluates the ECG data on a reduced set of leads by analyzing local features and/or global features of the ECG data. Local features may include local morphological measures such as ST elevation and clinical information on the patient such as age and sex. Global features include projection coefficients calculated from projecting a concatenated vector of heartbeat data onto separate sets of basis vectors that define signal subspaces of ischemic and non-ischemic ECGs. One or more classifiers evaluate the local features and/or global features to determine whether an acute cardiac ischemic condition is detected. The operating point, i.e., sensitivity and specificity, of the reduced lead set device is adjustable. The result of the evaluation is reported to the user of the device.

52 Claims, 22 Drawing Sheets

U.S. PATENT DOCUMENTS

| | | |
|---|---|---|
| 5,330,504 | 7/1994 | Somerville et al. . |
| 5,339,820 | 8/1994 | Henry et al. . |
| 5,365,426 | 11/1994 | Siegel et al. . |
| 5,365,932 | 11/1994 | Greenhut . |
| 5,365,935 | 11/1994 | Righter et al. . |
| 5,410,473 | 4/1995 | Kaneko et al. . |
| 5,413,592 | 5/1995 | Schroeppel . |
| 5,419,337 | 5/1995 | Dempsey et al. . |
| 5,456,261 | 10/1995 | Luczyk . |
| 5,470,342 | 11/1995 | Mann et al. . |
| 5,520,191 | 5/1996 | Karlsson et al. . |
| 5,554,175 | 9/1996 | Alferness . |
| 6,038,469 * | 3/2000 | Karlsson et al. .......... 600/509 |

* cited by examiner

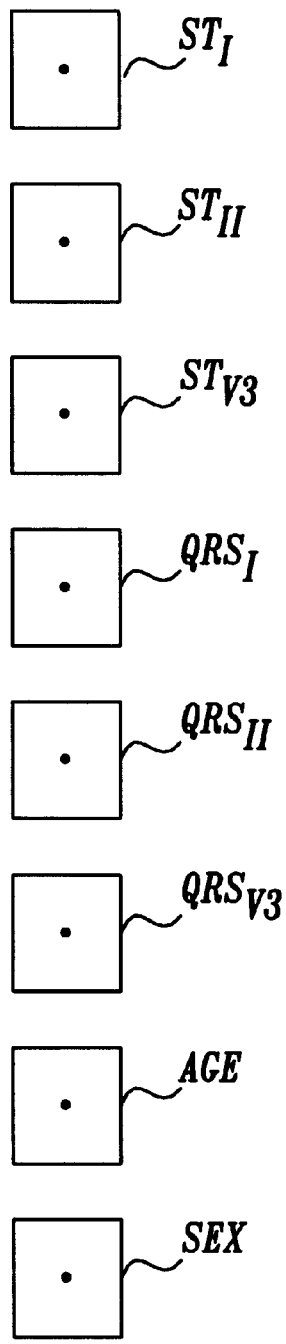
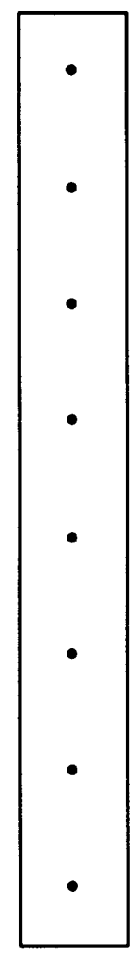
LOCAL FEATURES      FEATURE VECTOR $\underline{f}$
*Fig. 10A.*    *Fig. 10B.*

REPRESENTATIVE HEARTBEAT DATA

REPRESENTATIVE HEARTBEAT VECTOR $\underline{X}$

MATRIX V

MATRIX Λ

FEATURE VECTOR f

ISCHEMIA SUBSPACE

NON-ISCHEMIA SUBSPACE

PROJECTION COEFFICIENTS (GLOBAL FEATURES)

REDUCED LEAD SET DEVICE AND METHOD FOR DETECTING ACUTE CARDIAC ISCHEMIC CONDITIONS

RELATED APPLICATIONS

This application claims the benefit of U.S. provisional application Ser. No. 60/083,722 filed Apr. 30, 1998 and U.S. provisional application Ser. No. 60/100,391 filed Sep. 15, 1998, and is a continuation-in-part of U.S. application Ser. No. 09/209,879, filed Dec. 11, 1998, the benefit of the filing date of which is claimed under 35 U.S.C. §120.

FIELD OF THE INVENTION

The present invention relates generally to the analysis of cardiac electrical activity, and more specifically, to the evaluation of electrocardiogram data measured on a reduced set of leads to detect and report cardiac abnormalities.

BACKGROUND OF THE INVENTION

A variety of physiological processes are electrically mediated and produce associated electrical signals. For example, the sinoatrial node in a human heart generates an electrical pulse that triggers the remainder of a heartbeat in a normally functioning heart. This pulse propagates through the heart's normal conduction pathways producing electrical signals that can be observed on the surface of a patient's body. Analysis of such electrical signals has proved beneficial in evaluating the function of a patient's heart, including the detection of conditions associated with acute cardiac ischemia.

Analysis of a patient's cardiac electrical activity for detection of acute cardiac ischemic conditions is conventionally performed in a hospital setting using a 12-lead electrocardiogram (ECG) system. A conventional 12-lead ECG system measures voltage potentials sensed by ten electrodes attached to a patient and generates twelve combinations of these voltages to produce the "leads" required by the 12-lead ECG system. Of the ten electrodes in a 12-lead ECG system, four are "limb" electrodes typically placed on or near each of a patient's four limbs, and six are "precordial" electrodes positioned on the patient's chest over the heart. As an electrical impulse propagates through the heart, the ECG system repetitively measures the voltages sensed by the electrodes. Although the electrodes collectively measure the same cardiac electrical activity, the electrodes sense different voltages due to their different position on the patient with respect to the patient's heart. A time sequence of measured voltages is used to produce ECG lead data. An ECG system typically plots this data to provide graphical waveforms representing the heart's electrical activity for each lead being measured.

An example of an ECG waveform for a period of one cardiac cycle, or heartbeat, is shown in FIG. 1. The portion of a waveform representing depolarization of the atrial muscle fibers is referred to as the "P" wave. Depolarization of the ventricular muscle fibers is collectively represented by the "Q." "R," and "S" waves of the waveform. The portion of the waveform representing repolarization of the ventricular muscle fibers is known as the "T" wave. Between heartbeats, an ECG waveform returns to an "isopotential" line.

FIG. 1 also illustrates selected fiducial points labeled "q", "j", "t1", and "t2". Fiducial points define the boundaries of selected features and are used in measuring characteristics of an ECG waveform, such as the start and end of a heartbeat and the elevation of the ST portion of a heartbeat. The "q" point shown in FIG. 1 represents the start of the Q wave, the "j" point represents the end of the QRS complex, the "t1" point represents the start of the T wave, and the "t2" point represents the end of the T wave.

As noted, an analysis of a patient's ECG has proved beneficial in detecting acute cardiac ischemia in a patient. In terms of physiology, acute cardiac ischemia is a condition that arises from chronic or sudden onset of deprivation of blood, and hence oxygen, to muscles of the heart. If an ischemic condition is severe or prolonged, it can result in irreversible death or damage to myocardial cells (i.e., an infarction). A chronic cardiac ischemic condition, angina, is typically caused by narrowing of the coronary arteries due to spasms of the wall muscles or partial blockage by plaques. A sudden cardiac ischemic condition may be caused by a clot blocking the passage of blood in the coronary arteries. Symptoms of a cardiac ischemic event may include chest pain and pain radiating through the extremities, but not all such events present these symptoms. Current medical intervention for severe acute ischemic events includes the administration of a class of drugs called thrombolytics that dissolve clots in the occluded coronary artery, and emergent PTCA, a medical procedure that opens the artery by inflating a balloon inside the clot to make a passage for circulation.

Traditionally, acute cardiac ischemic conditions are detected in a hospital setting by a physician's visual evaluation of 12-lead ECG waveforms. A physician typically makes an assessment by comparing selected features of a patient's ECG waveforms with equivalent features of other persons' ECG waveforms that are representative of various abnormal conditions. A physician may also look at the patient's ECG waveforms over time and evaluate any changes in waveform shape. A number of waveform features have been identified as useful in diagnosing acute cardiac ischemic conditions. Customarily, a physician observes the extent to which the "ST" portion of a waveform exceeds the isopotential line (i.e., the ST elevation) and uses this information to determine if an acute ischemic event has occurred.

The amount of damage done to a heart by an ischemic event depends, in part, on the amount of time that lapses before treatment is provided. Therefore, ECG data should be evaluated as early as possible so that functional changes associated with cardiac ischemia can be detected and reported as early as possible. With early detection of acute cardiac ischemia, appropriate treatment can take place as early as possible and, thereby, maximize the preservation of myocardium. The American Heart Association recommends that a patient with suspected acute cardiac ischemia be evaluated by a physician using a 12-lead ECG within ten minutes of arrival at a hospital emergency department. Unfortunately, outside of a hospital, highly trained medical personnel are not always available to meet a patient's immediate needs. Quite often, a first responding caregiver to a patient in the field may be a lesser trained individual that is not competent in evaluating ECG waveforms to detect acute cardiac ischemic events.

Furthermore, it can be challenging for lesser trained individuals outside of a hospital to use a conventional 12-lead ECG system that requires proper placement of numerous electrodes on a patient's body. As noted earlier, a 12-lead ECG system requires ten electrodes to be spread across the chest and limbs of a patient. Serious misinterpretations may occur if the electrodes are incorrectly placed or connected. Lesser trained individuals may also have cultural inhibitions arising from placing electrodes at the required locations on the patient's chest. As a consequence, lesser trained individuals often delay obtaining ECG data for evaluating acute cardiac ischemic conditions until trained medical personnel are available. Each moment of delay, however, may seriously jeopardize the patient and result in further damage to the patient's cardiac tissue. A need, therefore, exists for a device that not only obtains ECG data in a simplified manner, but also quickly evaluates the ECG data and automatically produces a preliminary report of whether an acute cardiac ischemic condition has been detected.

While attempts have been made in some applications to reduce the number of electrodes required to obtain ECG data, these applications are generally directed to basic monitoring of a patient's heart rhythm for long-term patient observation and not for diagnosis of acute cardiac ischemic events. Devices for basic patient monitoring generally use a frequency response of about 0.5 to 40 Hz when at least three electrodes are connected. Devices for cardiac diagnosis generally have a wider frequency response of 0.05 to 150 Hz to maintain the full fidelity of the ECG without appreciable distortion. Furthermore, conventional ECG evaluation for diagnosing acute cardiac ischemia is more complex than basic patient monitoring; thus, the use of fewer than ten electrodes is discouraged, as such configurations provide a physician with fewer waveforms for analysis. The prior art has attempted to address this concern by using limited ECG data to approximate and extrapolate 12-lead ECG waveforms. Nevertheless, conventional ECG systems using fewer than ten electrodes are still perceived as providing a physician with an inadequate amount of data to accurately diagnose acute cardiac ischemia.

In recent years, there have been efforts to develop enhanced ECG waveform interpretation based on computer analysis. Conventional processes used for analyzing 12-lead ECG waveforms are typically based on heuristics derived from the experience of expert physicians. Such processes implement rules that attempt to simulate an expert physician's reasoning and therefore perform no better than the expert. In practice, many such processes often perform more poorly than human expert evaluation.

Furthermore, when a conventional heuristic process is used, it is often difficult to choose an optimal operating point for the device in terms of sensitivity (i.e., detecting true positives) and specificity (i.e., avoiding false positives). Generally speaking, a device tuned to be more sensitive is typically less specific, while a device tuned to be more specific is typically less sensitive. A typical sensitivity/specificity tradeoff is illustrated by a receiver operating characteristics (ROC) curve, an example of which is shown in FIG. 21. Using a conventional heuristic classifier, it is difficult to make the sensitivity/specificity tradeoff explicit; thus, the selection of an operating point on the ROC curve is often made in a suboptimal, ad hoc manner. As such, there is a need for a device and method that can provide better performance in terms of sensitivity and specificity and further provide for selecting a sensitivity/specificity tradeoff in a more systematic way.

Still further, a device and method are needed to decentralize the acquisition and evaluation of ECG data for acute cardiac ischemic conditions and provide a simpler and more accurate means for ECG evaluation that can be used by lesser trained individuals outside of a hospital. By providing analysis of ECG data further "out" from a hospital, earlier detection of acute cardiac ischemic conditions is anticipated, thus increasing the likelihood of survival of patients experiencing acute cardiac ischemic events. A device and method that use a reduced number of leads for automatic evaluation of ECG data for acute ischemic conditions are not known in the art. The present invention addresses these needs as well as other shortcomings in the prior art.

SUMMARY OF THE INVENTION

The present invention is a method and device that evaluates the electrical activity of a patient's heart using a reduced set of leads to automatically detect and report abnormalities associated with acute cardiac ischemia. The reduced set of leads are derived from ECG data obtained from a reduced number of electrodes (i.e., fewer than ten electrodes as used in a conventional 12-lead ECG system) placed on a patient. Consequently, the reduced set of leads contains fewer than the conventional 12 leads of ECG data obtained in a 12-lead ECG system.

A device employing the present invention is referred to herein as using a reduced lead set or being a reduced lead set device. ECG data acquired by a reduced lead set device formed in accordance with the present invention is analyzed for indications of acute cardiac ischemia by an acute cardiac ischemia detection process conducted by the device.

According to one aspect of the invention, the acute cardiac ischemia detection process analyzes selected local features derived from a patient to determine whether an acute cardiac ischemic condition is detected. Local features include measures of morphological features defined for a local time interval less than the duration of a representative heartbeat. An example of a local morphological feature is a measure of ST elevation derived from individual ECG lead data in the reduced set of leads. Clinical information, such as a patient's age and sex, may also be included in the analysis as local features. The local features are analyzed by a classifier implemented in the acute cardiac ischemia detection process.

In accordance with an alternative aspect of the invention, globally-distributed features extracted from the reduced set of leads are analyzed by an acute cardiac ischemia detection process. The globally-distributed features are derived from representative heartbeat data on each of the reduced number of leads by considering the representative heartbeat as a whole on each lead. The representative heartbeat data from each lead is concatenated to form a vector of representative heartbeat data for the reduced set of leads. The concatenated vector of representative heartbeat data is then mathematically projected onto predetermined basis vectors that define signal subspaces of ECGs exhibiting acute cardiac ischemic and non-ischemic conditions. The resulting projection coefficients are "global features" that are evaluated by a classifier to determine whether the global features are indicative of an acute cardiac ischemic condition.

In accordance with another aspect of the invention, the acute cardiac ischemia detection process evaluates both local features and global features obtained from the reduced set of leads for indications of acute cardiac ischemia. The local features and global features are either separately evaluated with the results combined, or evaluated in combination to produce a single result, yielding a final decision of whether an acute cardiac ischemic condition is present in the patient.

In accordance with other aspects of the invention, the reduced lead set device preferably has an adjustable sensitivity/specificity operating point. The sensitivity/specificity operating point is selected by adjusting a threshold in the classifier that determines the probability of detection of an acute cardiac ischemic condition. The sensitivity/specificity operating point of the reduced lead set device may be set by the manufacturer of the device, by the purchaser of the device, or by the user of the device. According to the invention, the reduced lead set device may also automatically adjust its sensitivity/specificity operating point based on the number of electrodes connected to the device. For example, when using a reduced number of electrodes, the reduced lead set device may set itself in a highly sensitive mode to detect all possible events indicating acute cardiac ischemia. If a potential acute cardiac ischemic event is detected, the reduced lead set device may prompt the user to attach additional electrodes to increase the number of available leads and repeat the detection process. With additional electrodes attached, the device may set itself to repeat the detection process with greater specificity to confirm the detection of acute cardiac ischemia in the patient. In this manner, the reduced lead set device can be used for screening as well as treatment decisions.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 10A is a pictorial diagram of selected local features derived from a patient;

FIG. 10B is a pictorial diagram of a concatenated feature vector $\underline{f}$ that includes the local features depicted in FIG. 10A;

DETAILED DESCRIPTION OF THE PREFERRED EMBODIMENT

The method and device of the present invention analyze a reduced set of ECG lead data to detect and report the presence of an acute cardiac ischemic condition in a patient. Preferably, the method and device analyze a subset of the leads normally acquired in a standard 12-lead ECG.

In regard to the present invention, acute cardiac ischemia includes conditions, both chronic and sudden, that result in a deprivation of blood, and hence oxygen, to the muscles of the heart, and thus require urgent treatment if the long-term viability of the cardiac muscle cells is to be maintained. While these conditions are reversible at the time of detection, these conditions will result in permanent damage to the cardiac muscle cells if sufficient blood flow is not restored.

As will be discussed in greater detail below, the invention includes an acute cardiac ischemia detection process that evaluates local features, global features, or a combination of local and global features, to detect acute cardiac ischemia. Prior to discussing the different aspects of the acute cardiac ischemia detection process, a detailed description of a reduced lead set device constructed according to the invention is provided.

I. Reduced Lead Set Device

Figure 2:
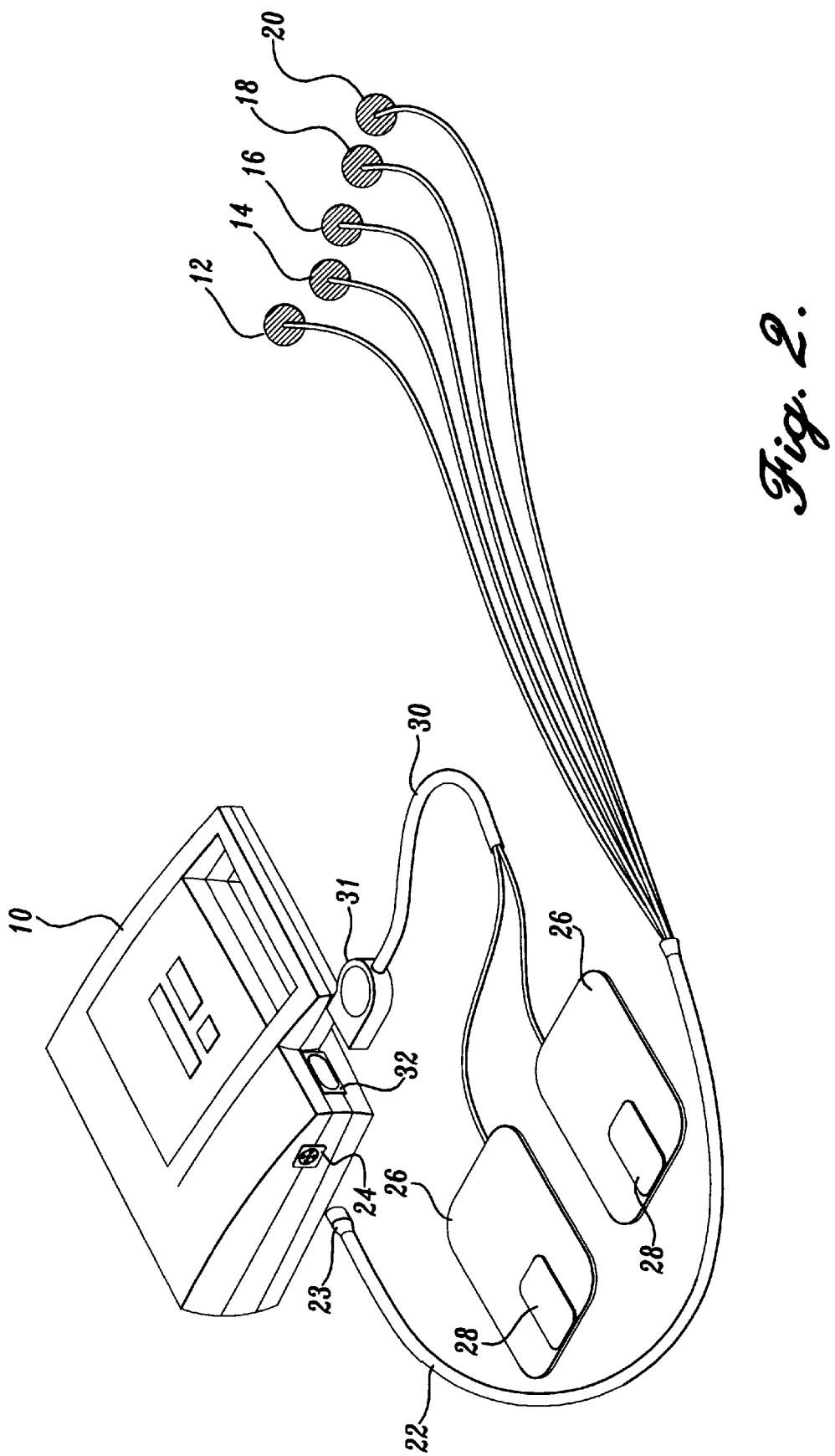
FIG. 2 depicts a reduced lead set device configured to operate in accordance with the present invention.

FIG. 2 depicts a reduced lead set device 10 constructed in accordance with the present invention. When attached to a patient via a plurality of electrodes (e.g., sensing electrodes 12, 14, 16, 18, and 20, or defibrillation electrodes 26, as shown in FIG. 2), the reduced lead set device 10 obtains ECG data from the patient, automatically evaluates the data, and reports whether an acute cardiac ischemic condition is present in the patient. The reduced lead set device 10 uses fewer electrodes than the number of electrodes required for a standard 12-lead ECG (i.e., less than ten electrodes). Consequently, the reduced lead set device 10 performs its analysis on a reduced set leads, or time series of voltage measurements, derived from the ECG signals sensed by the electrodes.

The sensing electrodes 12, 14, 16, 18, and 20 shown in FIG. 2 are connected to the reduced lead set device 10 via a cable 22 and a plug 23 that mates with an electrical connection receptacle 24 located on the device. While FIG. 2 shows five electrodes extending from the cable 22, greater or fewer than five electrodes may be used with the reduced lead set device 10, as will be better understood from the description below. The sensing electrodes 12, 14, 16, 18, and 20 are adapted for placement on the skin of a patient to sense the electrical activity of the patient's heart.

In one embodiment of the present invention, the reduced lead set device 10 is a stand-alone device dedicated to measuring and evaluating ECG signals. Alternatively, the device 10 may be integrated into another physiological instrument such as a defibrillator. In that regard, FIG. 2 depicts a pair of defibrillation electrodes 26 adapted for sensing a patient's ECG signals when not providing defibrillation therapy. The defibrillation electrodes 26 connect to the reduced lead set device 10 via a cable 30 and a plug 31 that mates with an electrical connection receptacle 32 located on the device 10. The pair of defibrillation electrodes 26 may include patches 28 that carry ECG sensing electrodes. The patches 28 are shown attached to one edge of the defibrillation electrodes 26 and fold outward from the defibrillation electrodes to contact the patient's skin when in use. Such patches increase the spatial distribution of ECG sensing electrodes while retaining a compact form when not in use. ECG sensing electrodes may also be embedded directly within the defibrillation electrodes 26, or the defibrillation electrodes 26 may include both embedded sensing electrodes and folding-patch sensing electrodes 28.

Although the reduced lead set device 10 shown in FIG. 2 includes separate electrical connection receptacles 24 and 32, the reduced lead set device may have a single electrical connection receptacle for either or both the sensing 12, 14, 16, 18, and 20, and the defibrillation electrodes 26. The electrodes and connection receptacles depicted in FIG. 2 are shown only for illustrative purposes. The reduced lead set device 10 may use a variety of electrode configurations to obtain ECG data from a patient.

Figure 3:
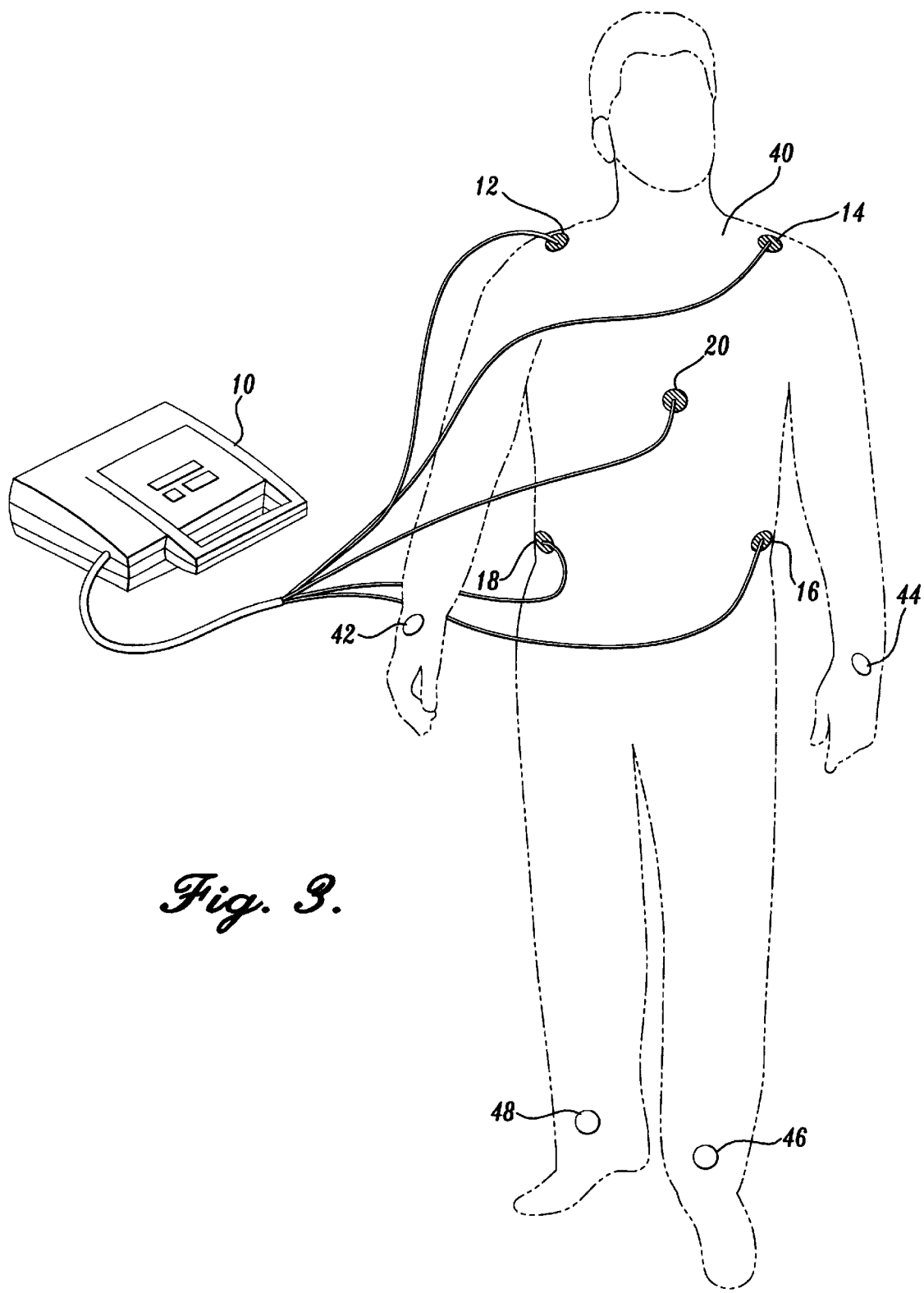
FIG. 3 depicts the reduced lead set device shown in FIG. 2 with five electrodes attached to a patient.

FIG. 3 depicts the reduced lead set device 10 shown in FIG. 2 attached to a patient 40 via the sensing electrodes 12, 14, 16, 18, and 20. The five electrodes are attached to the skin of the patient at a variety of locations. First and second sensing electrodes 12 and 14 are shown attached to the right and left shoulder areas of the patient 40. Third and fourth sensing electrode 16 and 18 are shown attached to the left and right side areas of the patient's torso near the patient's legs. A fifth sensing electrode 20 is shown attached to the patient's chest area over the heart.

Although FIG. 3 shows an electrode placement in accordance with one embodiment of the invention, it is appreciated that the electrodes of the reduced lead set device 10 may be placed alternative locations. For example, the limb electrodes 12, 14, 16, and 18 may be placed at the ends of the limbs of the patient 40 as indicated by the open circles 42, 44, 46, and 48, respectively. The limb electrodes 12, 14, 16, and 18 may also be placed at other locations on the patient's torso. The signals received from the sensing electrodes are used to produce ECG data in a manner well-known to those skilled in 12-lead ECG technology. Since the techniques for producing ECG lead data are well-known, a procedure for producing ECG lead data is not described here. Either electrode placement shown in FIG. 3 permits an analysis of a subset of the leads normally acquired in a standard 12-lead ECG, including the leads conventionally labeled I, II, III, V3, aVR, aVL, and aVF. One actual embodiment of the present invention obtains and analyzes leads I, II, and V3. Accordingly, for this embodiment of the invention, leads I, II, and V3 are otherwise referred to as the "available leads." It should be appreciated, however, that other leads, e.g., leads conventionally labeled III, aVR, aVF, aVL, V1, V2, V4, V5, and V6, may be selected and made available in other embodiments of the invention depending on the number and placement of electrodes used.

Figure 4:
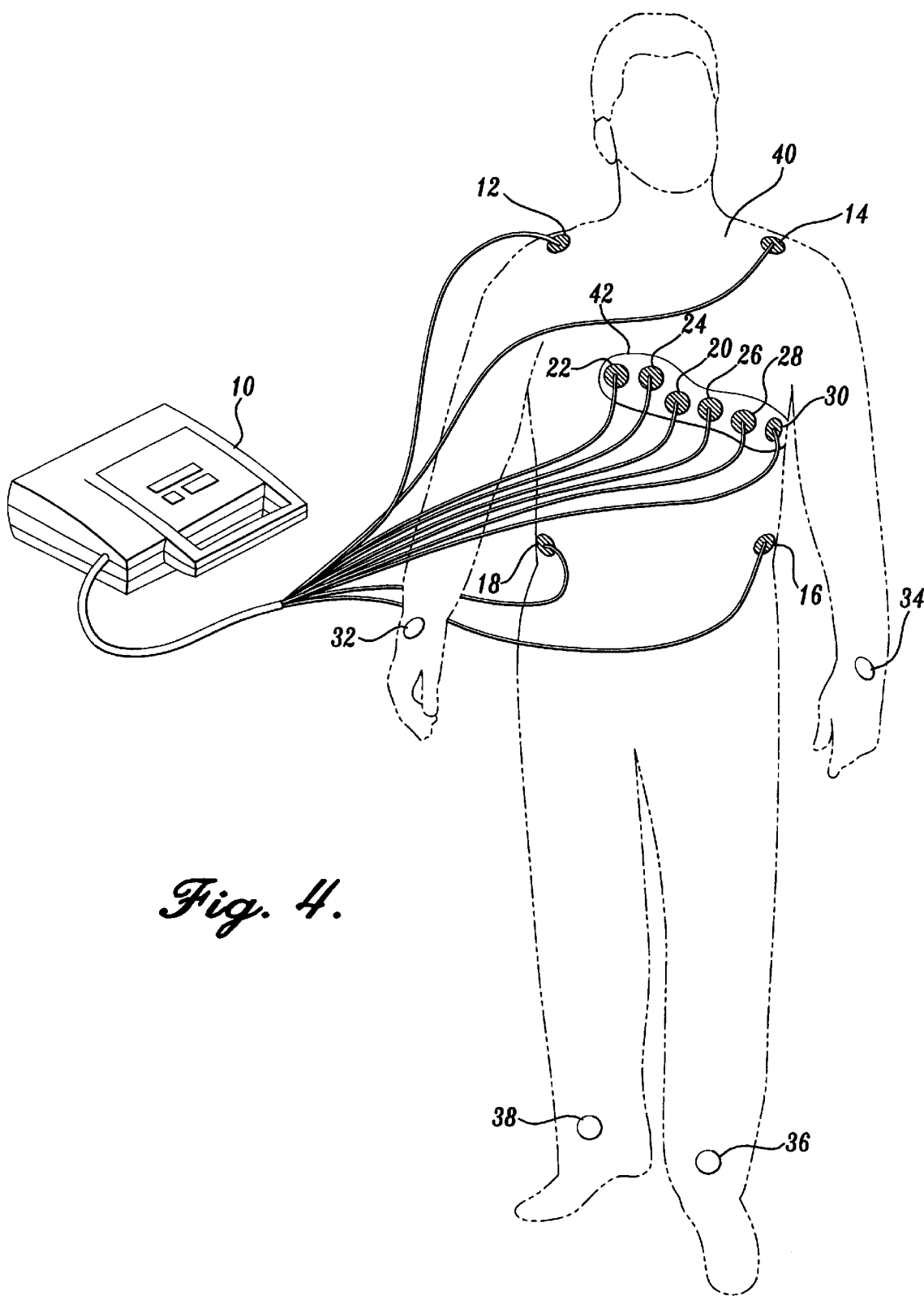
FIG. 4 depicts the reduced lead set device shown in FIG. 2 with ten electrodes attached to a patient.

Those skilled in ECG technology will appreciate that increasing the number of electrodes placed on the patient 40 increases the amount of ECG data that can be acquired from the patient. The additional ECG data obtained from an increased number of electrodes generally improves the ability of the reduced lead set device 10 to detect true acute cardiac ischemic conditions. FIG. 4 illustrates a configuration of the reduced lead set device 10 wherein five additional sensing 22, 24, 26, 28, and 30 have been added to the five electrode set illustrated in FIG. 3. The five additional sensing electrodes join electrode 20 and are spread across the chest of the patient 40. The ten electrodes shown in FIG. 4 are placed in the standard positions for a 12-lead ECG. For a user's convenience, the five additional sensing electrodes 22, 24, 26, 28, and 30, along with the electrode 20, may be individually attached to a patient's chest, or embodied in a single patch 42 that is placed on the patient's chest.

Figure 5:
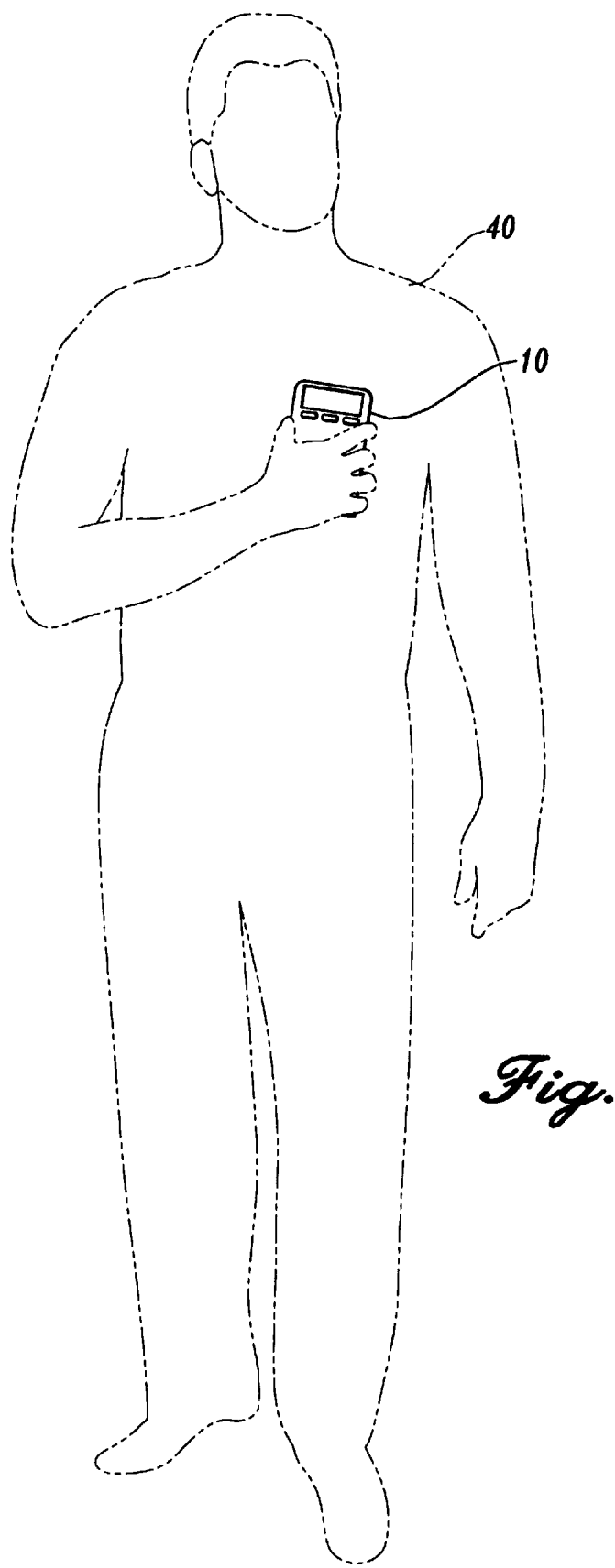
FIG. 5 depicts another embodiment of the reduced lead set device shown in FIG. 2 with a set of electrodes positioned on the back of the device that contact the patient's skin when held against the patient's chest as shown.

FIG. 5 depicts another embodiment of the reduced lead set device 10 wherein a reduced set of sensing electrodes positioned on the back of the device 10 (not visible in FIG. 5) contact the skin of the patient 40 when the device 10 is held against the patient's chest. Preferably, three or four electrodes are positioned on ha the back of the device 10. ECG lead data produced from the ECG signals sensed by the electrodes is analyzed by the device 10 in accordance with the present invention.

Figure 6:
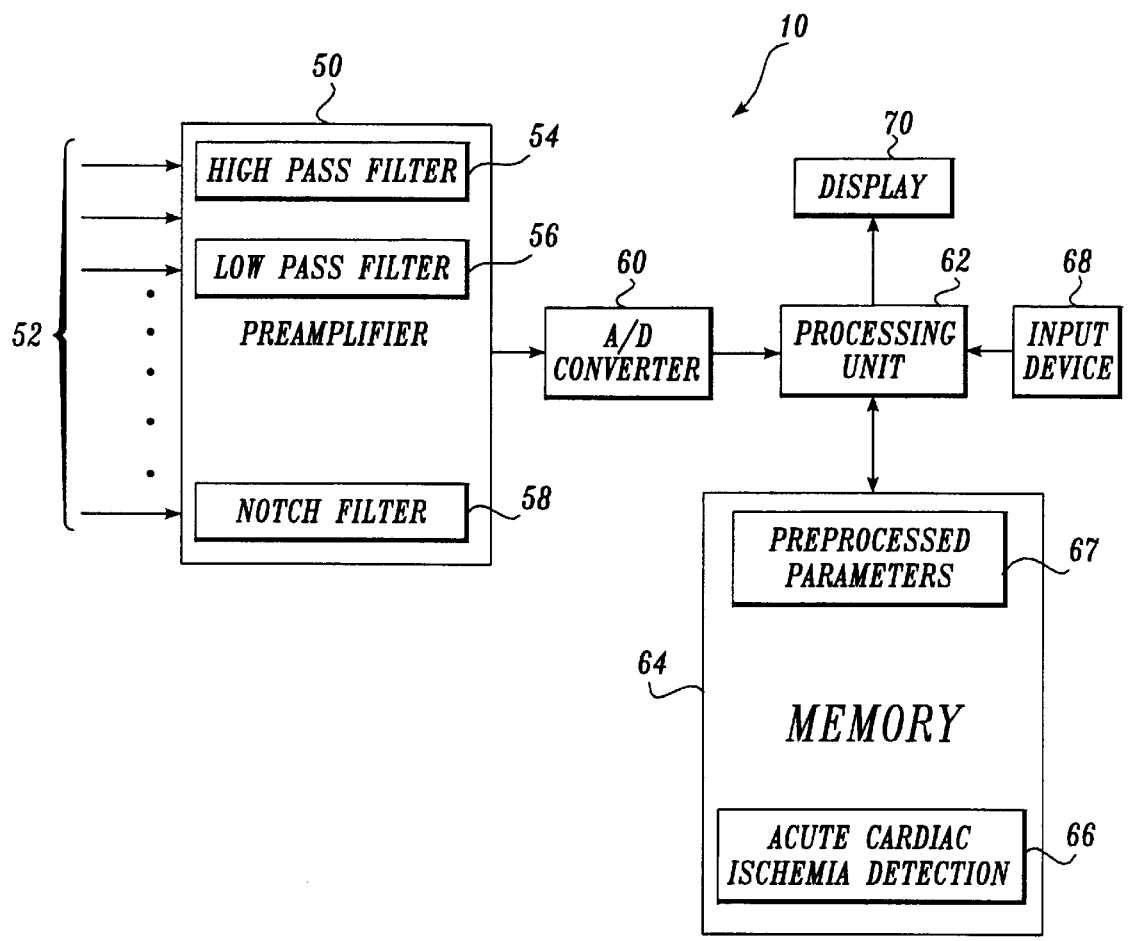
FIG. 6 is a block diagram of the major components of the reduced lead set device shown in FIG. 2.

FIG. 6 is a block diagram illustrating the major components of the reduced lead set device 10 shown in FIGS. 2–5.

ECG signals sensed by the sensing electrodes described above (not shown in FIG. 6) are communicated to a preamplifier 50 via lines 52. The preamplifier 50 both amplifies and filters the ECG signals. Amplification is required because the strength of the signals sensed by the electrodes is generally too low (i.e., in millivolts) to be analyzed by the circuitry of the reduced lead set device 10. The preamplifier 50 may amplify the ECG signals on lines 52 by a factor of 1,000 or more.

The amplified ECG signals are filtered to eliminate noise and other signal contaminants. In one actual embodiment of the invention, the filtering includes a high-pass filter 54 that attenuates low frequency signals (e.g., frequencies below 0.05 Hertz), a low-pass filter 56 that attenuates high frequency signals (e.g., frequencies above 150 Hertz), and a notch filter 58 that attenuates signals at a particular frequency (e.g., 50 or 60 Hertz, depending on the local line power frequency). Alternative embodiments of the present invention may include further signal filtering to adapt the reduced lead set device for use in a particular environment.

The amplified and filtered ECG signals are converted into digital ECG data by an analog-to-digital (A/D) converter 60. In the embodiment shown in FIG. 6, the ECG signals are multiplexed by the preamplifier 50 and serially communicated to the A/D converter 60. Alternatively, the ECG signals may be communicated in parallel from the preamplifier 50 to the A/D converter 60 via separate lines for each of the signals (not shown) and multiplexed by the A/D converter. Still further, a separate A/D converter may be provided for each amplified and filtered ECG signal and the output of the multiple A/D converters multiplexed.

The digital ECG data produced by the A/D converter(s) is communicated to a processing unit 62 for further processing and evaluation. A memory 64 in communication with the processing unit 62 stores the digital ECG data and other data subsequently generated by the acute cardiac ischemia detection process described in more detail below. The memory 64 stores an acute cardiac ischemia detection process 66 in the form of computer program instructions that, when executed by the processing unit 62, evaluates the digital ECG data and detects the occurrence of acute cardiac ischemia. The memory 64 also stores preprocessed parameters 67 derived earlier from patients in a training population during a training phase (described below). The preprocessed parameters 67 are used by the acute cardiac ischemia detection process 66 to evaluate the ECG of a current patient for acute cardiac ischemia.

Although analog signal filters 54, 56, and 58 are shown in FIG. 6 and described above, those skilled in the art will appreciate that, alternatively, digital filtering after the ECG signals are converted from analog form to digital form can be used, if desired. Furthermore, filtering of the ECG data can be performed after the data is stored in the memory 64, rather than being performed before storage, as shown.

FIG. 6 also depicts an input device 68 and a display 70 in communication with the processing unit 62 for exchanging information with a user of the reduced lead set device 10. The input device 68 allows a user to input information and selectively adjust the operation of the reduced lead set device while the display 70 allows the device to report the results of an ECG evaluation to the user. The display 70 also permits the reduced lead set device 10 to communicate instructions to the user.

Those of ordinary skill in the art will appreciate that various devices may be used to implement the function of the components shown in FIG. 6. For example, the processing unit 62 may be a microprocessor controlled by computer program instructions stored in the memory 64. The memory 64 may include nonvolatile memory in the form of read-only memory (e.g., EPROMs), storage memory (e.g., a hard drive), and/or volatile memory in the form of a random access memory (RAM). The input device 68 may include keys, dials, or switches. Similarly, the display 70 may be a combination of lights or a text display screen, e.g., AMLCD, LCD, or printer. Audible alerts may also be provided. The construction of suitable signal amplifiers, filters, and analog-to-digital converters are well-known to those having ordinary skill in the art and in many cases are readily available in off-the-shelf devices.

As part of an analog-to-digital conversion process, ECG signals sensed by the electrodes are sampled to obtain discrete voltage values at discrete time intervals. The rate at which the ECG signals are sampled depends on the configuration of the analog-to-digital converter 60. In one actual embodiment of the present invention, ECG signals are sampled at a rate of 500 samples per second. Those of ordinary skill in the art will appreciate that other sampling rates may be used.

As will be more readily understood from the discussion below, the reduced lead set device 10 not only acquires ECG data but also evaluates the data and reports whether conditions associated with acute cardiac ischemia are detected, including conditions that would lead to an acute myocardial infarction or unstable angina. According to one aspect of the invention, the reduced lead set device 10 evaluates local features obtained from representative heartbeat data on individual leads in the reduced set of leads. In accordance with an alternative aspect of the invention, the reduced lead set device 10 evaluates subtle, globally-distributed features derived from representative heartbeat data in the reduced set of leads. In yet another aspect of the present invention, the reduced lead set device 10 evaluates both local features and global features to determine whether an acute cardiac ischemic condition is present in the patient.

II. Acute Cardiac Ischemia Detection Using Local Features

Figure 7:
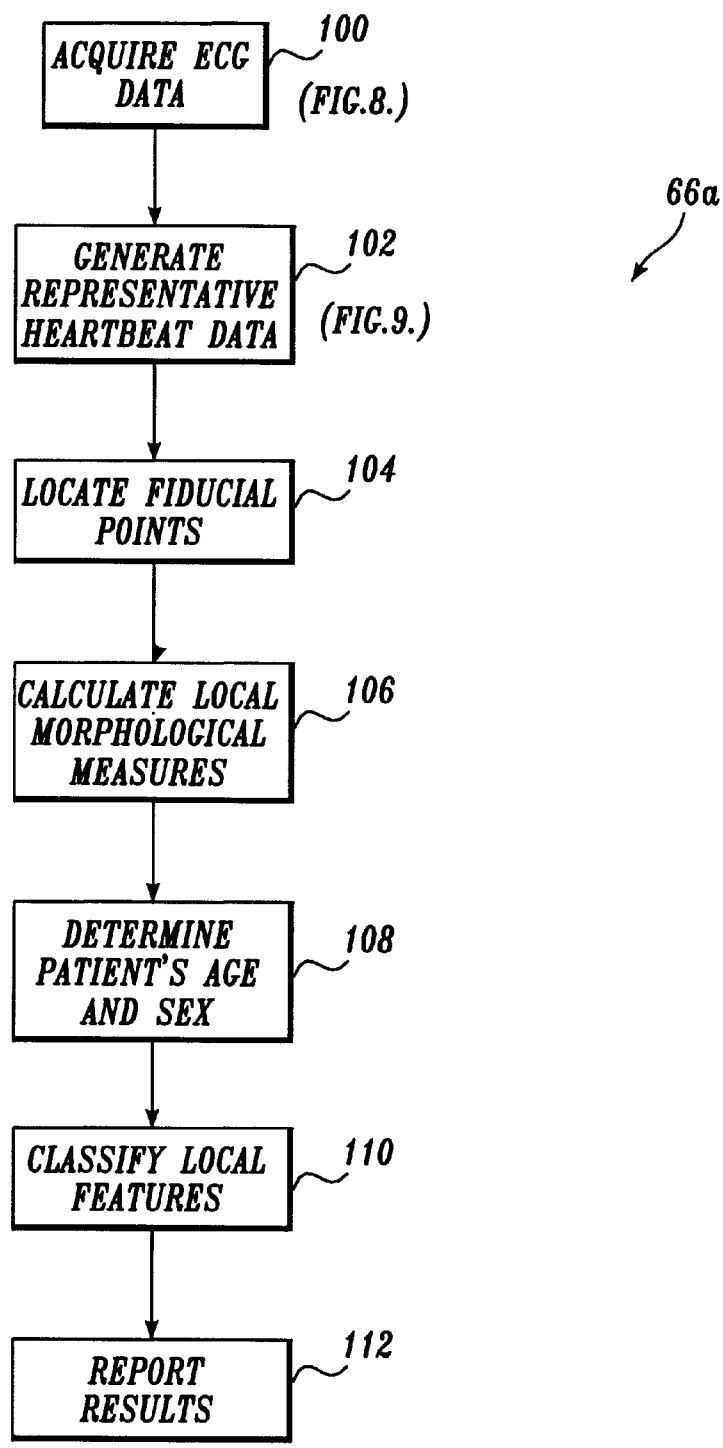
FIG. 7 is a flow diagram illustrating an acute cardiac ischemia detection process conducted by the reduced lead set device shown in FIGS. 2–6 which detects acute cardiac ischemic events by classifying local features derived from a patient.
Figure 8:
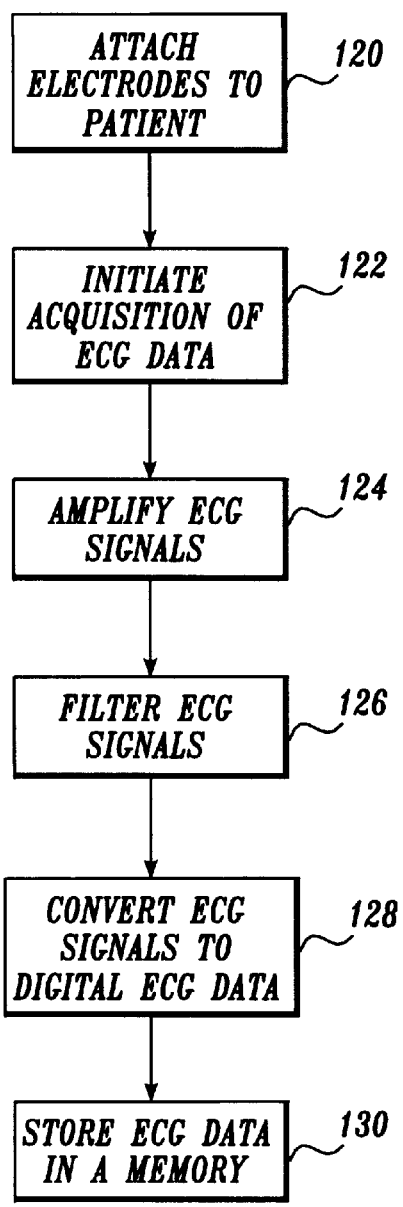
FIG. 8 is a flow diagram illustrating a process used to acquire ECG data for the acute cardiac ischemia detection process shown in FIG. 7.

FIG. 7 is a flow diagram illustrating a version of an acute cardiac ischemia detection process 66a that detects acute cardiac ischemia based on classifying local features. The detection process 66a includes both the determination of local features in blocks 100–108 and the classification of the local features in block 110. The detection process begins in a block 100 with the acquisition of ECG data from a patient. As illustrated more fully in FIG. 8, ECG data acquisition begins in a block 120 by attaching a reduced number of electrodes, such as the sensing electrodes 12, 14, 16, 18, and 20 shown in FIG. 3, to a patient 40. Once the electrodes are attached to a patient, the user of the reduced lead set device 10 initiates ECG data acquisition in a block 122 by initiating an input device 68, e.g., by pressing an ANALYZE button on the reduced lead set device. Alternatively, the reduced lead set device 10 may automatically initiate ECG data acquisition, e.g., upon expiration of a predetermined period of time counted by a timer that is started upon deployment or activation of the reduced lead set device. For a period of time thereafter, the voltage signals sensed by the electrodes are amplified in a block 124, filtered in a block 126, and converted to digital ECG data in a block 128, as discussed earlier in reference to the preamplifier 50 and the A/D converter 60 shown in FIG. 6. In a block 130, the ECG data is subsequently stored in the memory 64 of the reduced lead set device 10.

The period of time in which ECG data is acquired in block 100 of FIG. 7 is long enough to obtain sufficient, high-quality data representative of one or more heartbeats. In one actual embodiment of the present invention, the reduced lead set device 10 acquires about ten seconds of ECG data. This period of time may be increased or decreased depending on factors that affect the quality of the data acquired, including the quality of the connection between the electrodes and the patient, whether the patient is moving, and whether significant electromagnetic noise is present. Accordingly, depending on various factors, the period time for ECG acquisition may be increased to twenty seconds, or decreased to five seconds, for example, and still be considered an equivalent of about ten seconds of data for purposes of the subsequent processing discussed below.

After acquiring a patient's ECG data in block 100, the reduced lead set device 10 analyzes the ECG data and generates representative heartbeat data for each available lead in a block 102. Preferably, the representative heartbeat data represents an atrially-stimulated heartbeat that is common for the lead and is typically characterized by a high signal-to-noise ratio. If the acquired ECG data is of sufficient high quality, a single beat may be used for the representative heartbeat data. In most cases, however, it is preferable to combine two or more heartbeats on each lead to generate representative heartbeat data for the lead.

Figure 1:
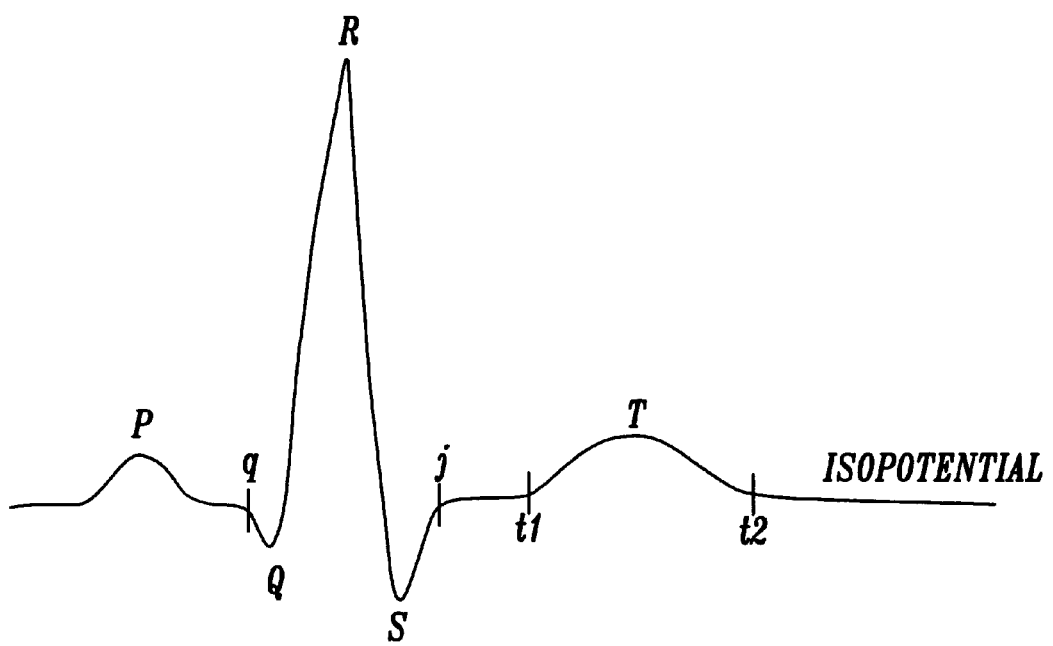
FIG. 1 illustrates an example of an ECG waveform corresponding to a single heartbeat.
Figure 9:
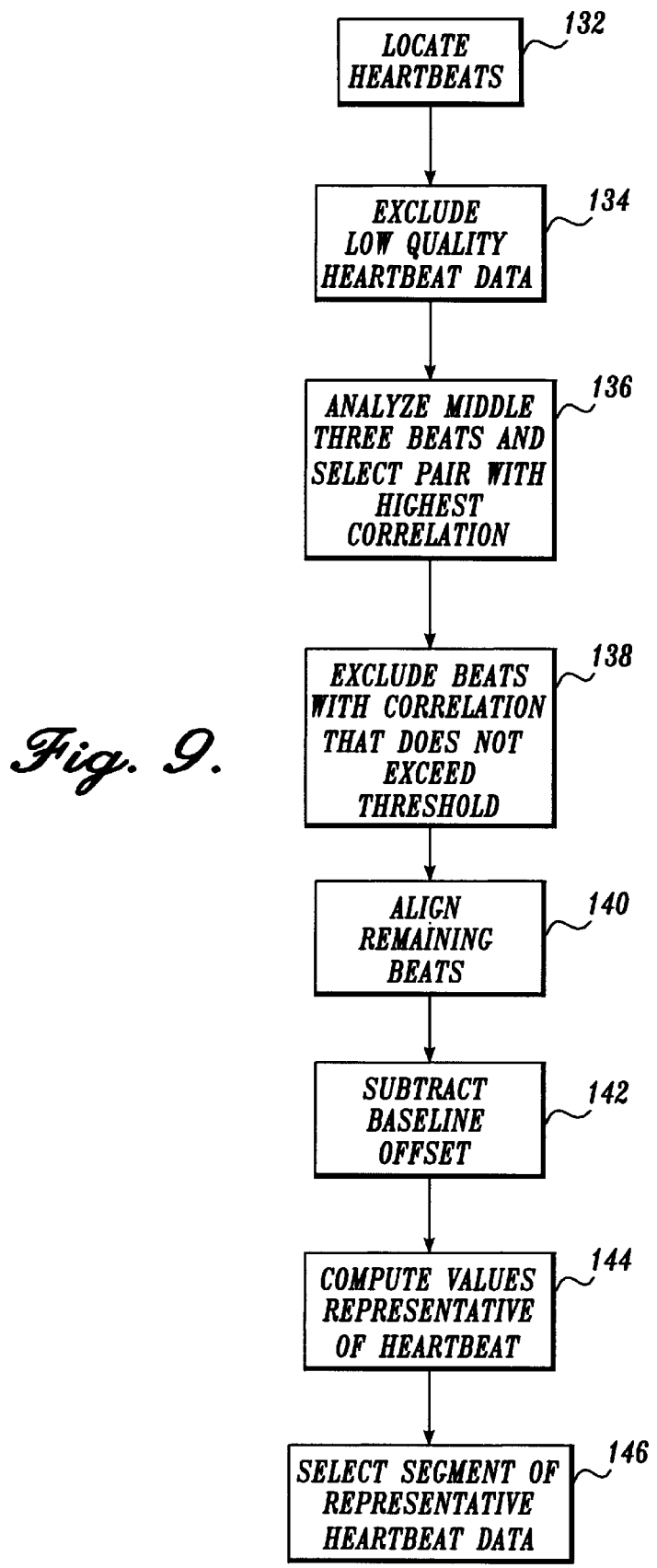
FIG. 9 is a flow diagram illustrating a process used to generate representative heartbeat data for the acute cardiac ischemia detection process shown in FIG. 7.

FIG. 9 illustrates in more detail a process for generating representative heartbeat data suitable for use in the present invention. In the process shown, multiple heartbeats on a lead are used to generate the representative heartbeat data for the lead. The reduced lead set device 10 first locates the heartbeats on each available lead, e.g., leads I, II, and V3 for one actual embodiment of the invention, in a block 132. In that regard, heartbeats may be located by detecting the dominant feature of the QRS complexes, i.e., the R waves (see FIG. 1), of each heartbeat. Because the quality of the representative heartbeat data is improved by selecting and using only high quality ECG data, the raw ECG data is analyzed in a block 134 to exclude low quality heartbeat data. For example, heartbeat data that exhibits significant noise content (e.g., data with energy values greater than one standard deviation away from the mean of the QRS energy values measured, for example, by a sum of squared values) is excluded in block 134 from further consideration for generating a representative heartbeat. Of the retained heartbeat data, the middle three heartbeats (middle in a temporal sense) are analyzed and two of the three heartbeats that have a highest pairwise cross-correlation are selected in a block 136 for further consideration. The non-selected third heartbeat is excluded from further consideration.

The retained heartbeats are then individually compared with the first heartbeat of the pair selected above. Specifically, a cross-correlation value is determined for each of the QRS complexes of the remaining heartbeats with respect to the first beat of the selected pair. Those heartbeats having a correlation value greater than a specified threshold value (e.g., 0.9 out of a perfect 1.0) are retained. The heartbeats having a lower correlation value are excluded in a block 138 from further consideration for generating a representative heartbeat. The heartbeats retained are used in generating a representative heartbeat for the lead being analyzed.

To generate a representative heartbeat for the lead, the waveforms of the retained heartbeats are aligned in a block 140 by matching up waveform features such as the R wave peak, preferably according to the maximum cross-correlation of data samples in the retained heartbeats. Further, a baseline offset calculated for each beat is subtracted in a block 142 from the data samples in each retained heartbeat. The baseline offset is the amount that the data samples in a heartbeat exceed a selected reference level. In an actual embodiment of the invention, the baseline offset is estimated as the mean of 48 milliseconds of ECG data taken from an 88 millisecond mark to a 40 millisecond mark prior to the QRS peak sample (e.g., if the QRS peak was located at the 100 millisecond mark, the estimated baseline offset is the mean of the samples from the 12 millisecond mark to the 60 millisecond mark). It is appreciated that more or less ECG data may be used, or the timing of the ECG segment used may be shifted, in calculating a baseline offset.

Next, in a block 144, a set of values representative of an average heartbeat for each available lead is calculated from the retained heartbeat data. In one actual embodiment of the invention, the representative heartbeat data is generated by calculating a sample-by-sample average of the retained heartbeats. Nevertheless, it is understood that a wide variety of mathematical operations may be used instead of averaging. For example, representative heartbeat data may be computed from a sample-by-sample mean, mode, weighted mean (using weighing coefficients), trimmed mean (i.e., calculate a mean or median from a set of values that excludes values that are too large or too small), or median.

Before the resulting representative heartbeat data is subjected to further evaluation, it may be advantageous to reduce the amount of data being evaluated. In that regard, data samples in a segment of the representative heartbeat data are selected in a block 146 to represent the ECG information of particular interest. In one actual embodiment of the present invention, a 480 millisecond segment of representative heartbeat data for each available lead is selected beginning at an 8 millisecond mark before each representative heartbeat's QRS peak. Data outside the selected segment is excluded from the further processing and evaluation performed. In reducing the amount of data being evaluated, it is appreciated that a segment of ECG data longer or shorter than 480 milliseconds may be selected. The beginning mark may also be adjusted earlier or later in the sequence of ECG data.

While the process shown in FIG. 9 is used to generate representative heartbeat data in one actual embodiment of the invention, it should be understood that other ones of the many known procedures for generating representative heartbeats can be used. For example, the methods of representative heartbeat generation used in the LIFEPAK® 11 or LIFEPAK® 12 defibrillators manufactured by Physio-Control Corporation of Redmond, Wash., may be used, if desired.

Returning again to FIG. 7, once the representative heartbeat data is generated for each available lead in block 102, the reduced lead set device 10 analyzes the representative heartbeat data in block 104 to locate the representative heartbeat's fiducial points. Fiducial points are used in measuring the local features of an ECG waveform.

After locating the fiducial points in block 104, the reduced lead set device 10 determines a set of local features to be evaluated for indications of an acute cardiac ischemic condition in the patient. Local features include, for example, local morphological measures calculated in a block 106 from the representative heartbeats of the patient, e.g., ST elevation, T wave amplitude, and QRS area measures. Local features may also include clinical information, such as the patient's age and sex, input in a block 108 into the reduced lead set device 10 by the user of the device. With regard to sex information, a "1" may be used for males and a "0" may be used for females. If clinical information is not entered at this time, default values may be used. While information such as age and sex may help improve the accuracy of the classification performed to detect acute cardiac ischemia, the acute cardiac ischemia detection process 66a of the present invention can be performed without this information.

The local morphological measures and patient clinical information thus obtained (i.e., the local features) are input into a classifier in a block 110 that determines whether the local features are indicative of a condition associated with acute cardiac ischemia. The determination made by the classifier is reported in a block 112 to the user of the reduced lead set device 10.

The classifier in block 110 may be either a heuristic classifier (based on an expert system) or a statistical classifier. A heuristic classifier mimics procedures used by an expert (i.e., a cardiologist) to evaluate an ECG and report a preliminary determination. A heuristic classifier uses programmed rules to compare the local features to expert-determined thresholds and determine whether an acute cardiac ischemic event has occurred. The programmed rules are stored as processed parameters 67 in the memory 64 shown in FIG. 6. For an expanded description of how to construct a suitable heuristic classifier for use in this aspect of the invention, see G. Wagner, *Marriott's Practical Electrophysiology*, 9th Ed. (1994), published by Williams & Wilkins, Baltimore, which is incorporated herein by reference.

In contrast to a heuristic classifier which relies upon expert-defined rules, a statistical classifier develops its own classification rules during a training phase. Statistical classifiers may use, for example, the techniques of multivariate regression, k-nearest neighbor procedures, discriminate analysis, as well as neural network techniques. Using local features drawn from representative training populations, a statistical classifier is trained to associate particular patterns in the local features with clinical outcomes of interest. For example, a statistical classifier in this regard is trained with data derived from an ischemic training population and a non-ischemic training population to identify patterns of local features associated with acute cardiac ischemia. The output of a statistical classifier is a classification statistic that is compared with a numerical threshold to yield a final decision, e.g., whether or not acute cardiac ischemia is present. For example, a classifier producing an output that is less than a numerical threshold "t" may classify the local features as belonging to an ischemic class, while producing an output that exceeds the threshold "t" may result in classifying the local features in a non-ischemic class. For an expanded description of statistical classifiers suitable for use in evaluating local features, including descriptions as to the manner in which threshold values may be determined, see R. Duda and P. Hart, *Pattern Classification and Scene Analysis* (1973), published by John Wiley & Sons, New York, which is incorporated herein by reference.

One statistical classifier suitable for use in the present invention involves comparing the set of local features derived from the patient with corresponding mean local features derived during an earlier training phase from a training population of patients. An example of a set of local features is shown in FIG. 10A in which dots are used to indicate numerical values. The set of local features in FIG. 10A includes an ST elevation measure for each of the available leads in the reduced set of leads (e.g., leads I, II, and V3). The set of local features also includes a QRS area measure for each of the leads and the patient's age and sex information.

To understand a statistical classifier used to classify the local features, it is first necessary to understand the training phase used to train the classifier. For purposes of discussion herein, patients in a training population of patients known to have acute cardiac ischemia are referred to as ischemic training patients or an ischemic training population. Likewise, patients in a training population of patients known to not have acute cardiac ischemia are referred to as non-ischemic training patients or a non-ischemic training population.

Figure 11:
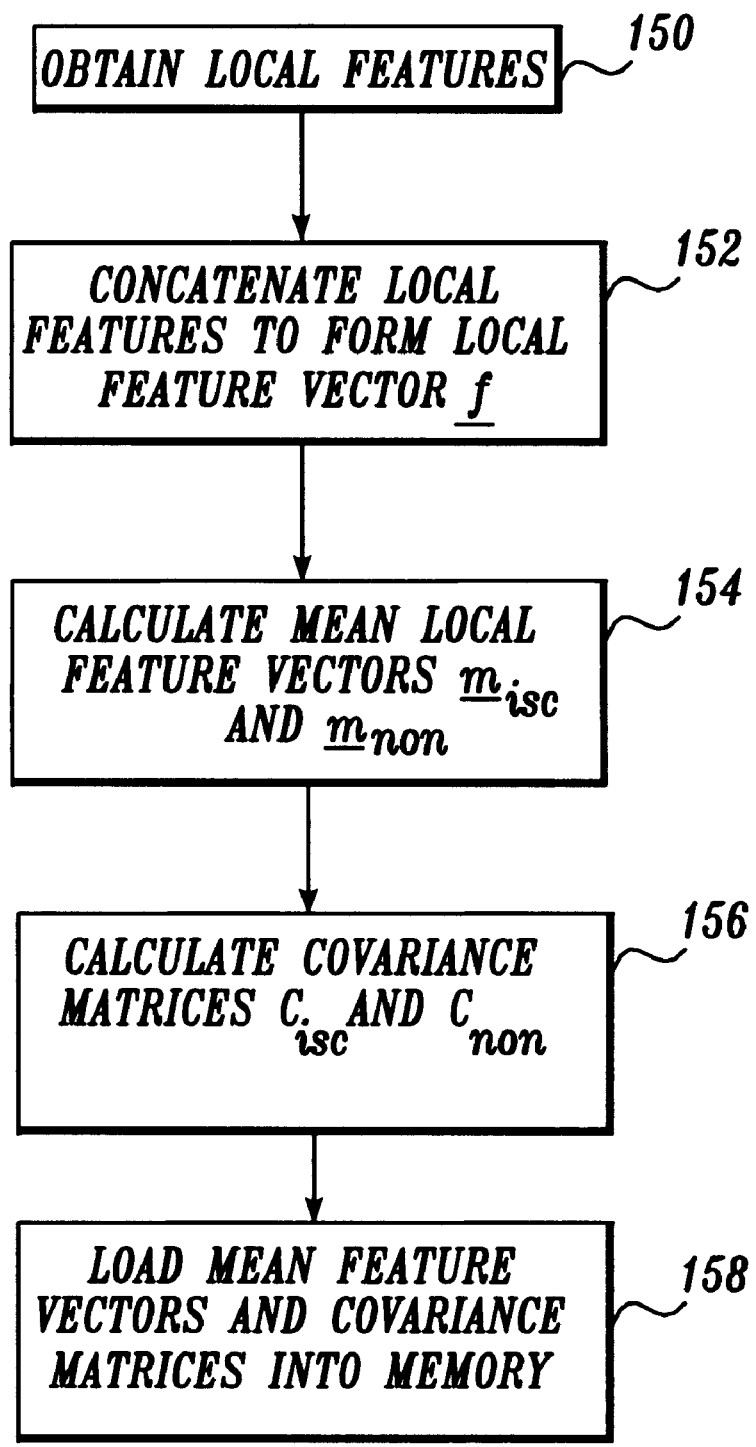
FIG. 11 is a flow diagram illustrating a process performed during a training phase to derive a set of classifier parameters used by the acute cardiac ischemia detection process shown in FIG. 7.

Referring to FIG. 11, during the training phase, a set of local features is obtained in a block 150 from each of the ischemic and non-ischemic training patients. For each training patient, the local features are concatenated in block 152 to form individual local feature vectors $\underline{f}$. An example of a feature vector $\underline{f}$ is shown in FIG. 10B. In a block 154, mean feature vectors $\underline{m}_{isc}$ and $\underline{m}_{non}$ are subsequently calculated for the ischemic and non-ischemic training populations, respectively, by computing a feature-by-feature mean of all of the individual local feature vectors $\underline{f}$ of the patients in the respective training populations. In a configuration where a set of eight local features are obtained from a patent, as shown in FIG. 10A, the concatenated feature vectors $\underline{f}$ (FIG. 10B), and thus the mean feature vectors $\underline{m}_{isc}$ and $\underline{m}_{non}$, will include eight values.

In a block 156, a covariance matrices $C_{isc}$ and $C_{non}$ are also calculated in a block 156 for the ischemic and non-ischemic populations, respectively. Generally speaking, a covariance matrix C contains the statistical covariance of the feature vectors $\underline{f}$ of the respective training population with respect to the calculated mean feature vector $\underline{m}$ for the population. The covariance matrix C is calculated for a population of N patients as follows:

$$C = \frac{1}{N}\sum_{i=1}^{N}\left((\underline{f}_i - \underline{m})(\underline{f}_i - \underline{m})^T\right) \qquad (1)$$

Covariance matrices $C_{isc}$ and $C_{non}$ produced by Equation (1) provides an indication of how widely dispersed the local features of the ischemic training patents and the non-ischemic training patients were from the calculated mean local features for the respective populations. The mean feature vectors $\underline{m}_{isc}$ and $\underline{m}_{non}$, and the covariance matrices $C_{isc}$ and $C_{non}$ thus calculated are stored in a block 158 as preprocessed parameters 67 in memory 64 (FIG. 6) for later use in classifying the current patient's local features.

The statistical classifier in block 110 (FIG. 7) evaluates the current patient's local feature vector $\underline{f}$ with respect to the mean local feature vectors $\underline{m}_{isc}$ and $\underline{m}_{non}$ and covariance matrices $C_{isc}$ and $C_{non}$ according to the following general equation:

$$d = \sqrt{(\underline{f}-\underline{m})^T C^{-1} (\underline{f}-\underline{m})} \qquad (2)$$

A quantity $d_{isc}$ computed from Equation (2) reflects the distance between the current patient's local feature vector $\underline{f}$ and the mean local feature vector $\underline{m}_{isc}$ weighted by a covariance matrix $C_{isc}$ for the ischemic population. Similarly, a quantity $d_{non}$ reflects the distance between the current patient's local feature vector $\underline{f}$ and the mean local feature vector $\underline{m}_{non}$ relative to the covariance matrix $C_{non}$ for the non-ischemic population. The statistical classifier in block 110 compares the quantities $d_{isc}$ and $d_{non}$, and if $d_{isc}$ is less than $d_{non}$, an acute cardiac ischemic condition is detected and reported. It is appreciated that alternative distance metrics may be calculated for comparing a patient's local feature vector $\underline{f}$ with a mean local feature vector $\underline{m}$.

In Equation (2), the covariance matrix C is inverted so that if a mean local feature in the vector m has a corresponding high covariance, any deviation of the patient's corresponding local feature from the mean local feature is not weighted as greatly as a situation wherein the mean local feature has a low covariance. Thus, if a particular local feature of a patient deviates significantly from a corresponding mean local feature having a low covariance, greater attention is drawn to the patient's deviation on that feature by giving greater weight to the resultant value.

For purposes of discussion herein, it is presumed that the statistical classifier in block 110 uses a distance metric that reports the detection of acute cardiac ischemia if $d_{isc}$ is less than $d_{non}$. In other words, if $d_{non} > d_{isc}$, a detection of acute cardiac ischemia is reported. From the foregoing, it follows that if $d_{non} - d_{isc} > 0$, a detection of acute cardiac ischemia is reported. The computed quantity on the left side of the latter inequality is called a classification statistic. The value "0" on the right side of the latter inequality is a decision threshold against which the classification statistic is compared. More generally stated, if $d_{non} - d_{isc} > t$, where "t" is the decision threshold, acute cardiac ischemia is reported. As will be discussed below in reference to FIG. 21, the sensitivity/specificity tradeoff of the reduced lead set device 10 may be adjusted by varying the threshold "t."

As an alternative, or in addition to evaluating a patient's local morphological measures and clinical information as local features, one or more composite local features derived from the local morphological measures and clinical information may be calculated and input into the classifier in block 110. In one actual embodiment of the invention, two different procedures are used for calculating composite local features. One procedure involves using a logistic regression equation to produce a preliminary prediction of whether acute cardiac ischemia is present. The logistic regression equation is derived earlier during a training phase according to a logistic regression model defined by the following equation.

$$\log\left(\frac{p}{1-p}\right) = a_0 + \sum_{i=1}^{K} a_i x_i \quad (3)$$

In Equation (3), "p" denotes the probability of detected acute cardiac ischemia, $a_o$ is a calculated constant, $a_i$ denotes the calculated $i^{th}$ regression coefficient, and $x_i$ denotes the $i^{th}$ explanatory variable (in this case, the local features of a patient). During the training phase, the probability of detected acute cardiac ischemia is known (i.e., the probability of ischemia is 1 for the ischemic training population and the probability of ischemia is 0 for the non-ischemic training population). Using the known probability information and the local features of the patients in the respective training populations, the regression coefficients of the logistic regression equation are determined in accordance with Equation (3). The regression coefficients are stored as preprocessed parameters 67 in the memory 64 (FIG. 6) for later use in producing a probability of detected acute cardiac ischemia in the patient under current evaluation.

For the patient under current evaluation, the patient's local features are input into the logistic regression equation derived during the training phase described above. More specifically, the patient's local features are weighted by the derived regression coefficients and combined as shown in Equation (3) to produce an output "p." The output "p" (i.e., the probability of detected acute cardiac ischemia) is used as a composite local feature to be classified in the classifier in block 110.

Alternatively, rather than directly inputting the composite local feature into the classifier in block 110, it may be advantageous to first dichotomize the composite local feature. For instance, if the composite local feature exceeds a preselected threshold, the composite local feature is assigned a value of "1" (indicating predicted acute cardiac ischemia). If the composite local feature does not exceed the threshold, it is assigned a value of "0" (indicating predicted non-ischemia). The threshold used to dichotomize the composite local feature is selected based on prediction patterns observed in the training populations during the training phase. The dichotomized composite local feature is then input into the classifier in block 110. For additional description of suitable logistic regression models, see D. Hosmer and S. Lemeshow, *Applied Logistic Regression* (1989), John Wiley & Sons, New York, incorporated by reference herein.

Another procedure for creating a composite local feature involves calculating a Mahalanobis distance. A Mahalanobis distance "d" is calculated according to Equation (2) and measures the distance between the patient's set of local features and a representative set of local features derived from a training population. A Mahalanobis distance $d_{isc}$ and/or $d_{non}$, calculated using representative local features from ischemic and/or non-ischemic training populations, may be provided as composite local features to the classifier in block 110. More than one composite local feature may be provided to the classifier in block 110, including a dichotomized composite local feature derived by logistic regression and a composite local feature derived from calculating a Mahalanobis distance.

The preceding discussion in connection with FIGS. 7–11 describes one aspect of the present invention where classification of local features derived from a reduced set of leads is performed. In another aspect of the present invention, the reduced lead set device 10 may alternatively perform a global classification evaluation. As will be better understood from the discussion below, a global classification evaluation involves concatenating representative heartbeat data calculated from the reduced set of leads, extracting global features from the concatenated representative heartbeat data, and determining whether the global features are indicative of acute cardiac ischemia. More specifically, the global classification evaluation involves mathematically projecting a concatenated vector of representative heartbeat data onto predetermined basis vectors that define an acute cardiac ischemic ECG subspace and onto predetermined basis vectors that define a non-ischemic ECG subspace. The resulting projection coefficients are the global features that are classified to determine whether a presence of an acute cardiac ischemic condition is detected.

Acute Cardiac Ischemia Detection Using Global Features

Figure 12:
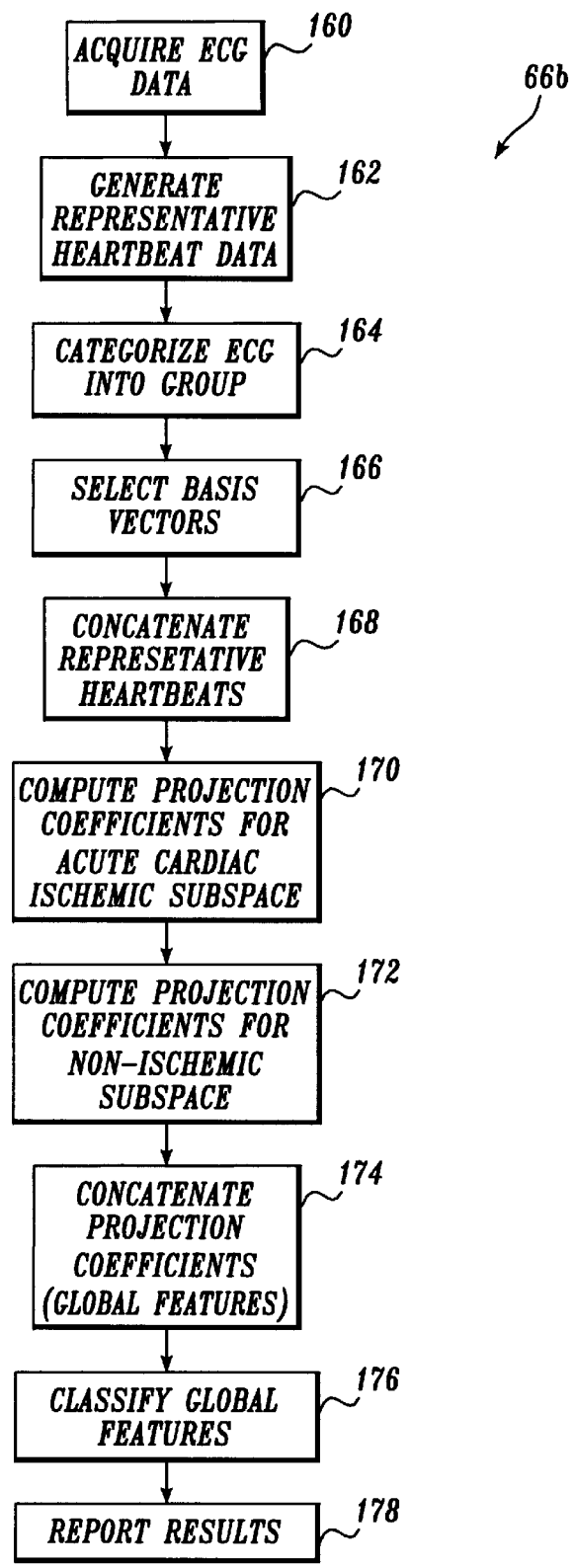
FIG. 12 is a flow diagram illustrating an alternative acute cardiac ischemia detection process conducted by the reduced lead set device shown in FIGS. 2–6 which detects acute cardiac ischemic events by classifying global features derived from a patient's ECG.

FIG. 12 is a flow diagram illustrating another version of an acute cardiac ischemia detection process 66b formed in accordance with the present invention wherein global features are derived and classified to determine the presence of acute cardiac ischemia. In the manner described earlier in reference to FIGS. 7–9, in a block 160 the reduced lead set device 10 acquires about ten seconds of ECG data that is amplified and filtered. In a block 162, the reduced lead set device 10 then generates representative heartbeat data for each of the available leads.

While the representative heartbeat data for each lead may be reduced to a 480 millisecond segment of data, as described earlier in reference to block 146 of FIG. 9, it is again noted that a segment of any length (preferably containing, at least, the QRST portions of the ECG) may be used. Nevertheless, as will be better understood from the discussion below, a fixed number of samples in a representative heartbeat must be set a priori during the training phase for the later performed global classification evaluation of the present invention. The length of the basis vectors derived during the training phase and later used in the global classification evaluation depends on both the number of data samples in each representative heartbeat and the number of available leads in the reduced set of leads.

As a matter of background, prior to discussing the global classification evaluation illustrated in blocks 164–176 of FIG. 12, a discussion of some concepts underlying the global classification evaluation is provided. Following that discussion, a description of the training phase required to derive the basis vectors is provided.

One concept underlying the global classification evaluation shown in FIG. 12 is that a series of numbers can be viewed as the coefficients of a vector that defines a point in a multidimensional signal space. In the case of the present invention, this means that a series of ECG data points in a patient's representative heartbeat may be viewed as the coefficients of a vector defining a point in a multidimensional ECG signal space. The number of dimensions in the ECG signal space is determined by the number of data points in the patient's representative heartbeat data subject to evaluation. In a similar manner, a series of global features derived from a patient's ECG according to the invention may be viewed as the coefficients of a vector defining a point in a multidimensional feature space. The number of dimensions in the feature space is determined by the number of global features derived from the patient's ECG. It should be understood that the ECG signal space and the feature space discussed above are completely different conceptual spaces, though in regard to this aspect of the invention, they are related by virtue of the projecting operation described below in reference to blocks 170 and 172 of FIG. 12.

Sets of global features derived from the ECG data of patients in an ischemic training population may be plotted as points defining an "ischemic" region of the feature space. In a similar fashion, sets of global features derived from the ECG data of patients in a non-ischemic training population may be plotted as points defining a "non-ischemic" region of the feature space. According to the present invention, if a set of global features derived from the ECG data of a patient under current evaluation defines a point in the feature space closer to the ischemic region than the non-ischemic region, the reduced lead set device 10 reports the detection of acute cardiac ischemia. The threshold of "closeness" for detecting acute cardiac ischemia is adjustable, thus providing the reduced lead set device 10 with an adjustable sensitivity/specificity tradeoff, as will be discussed in more detail below.

Within the ECG signal space (which, as noted, is different than the feature space), ECG data obtained from ischemic training patients is viewed as defining an ischemic ECG subspace. Likewise, ECG data obtained from non-ischemic training patients is viewed as defining a non-ischemic ECG subspace. The ischemic and non-ischemic ECG subspaces may be succinctly characterized by mathematical basis vectors that are derived in a training phase. The basis vectors are stored as preprocessed parameters 67 in memory 64 of the device 10. As will be discussed later in greater detail, the basis vectors are used in blocks 170 and 172 of FIG. 12 to derive the projection coefficients (i.e., global features) of the patient under current evaluation.

Before deriving a set of basis vectors to characterize each of the ischemic and non-ischemic ECG subspaces, the quality of this characterization may be enhanced by dividing the ischemic and non-ischemic training populations into smaller groups according to a selected characteristic. Sets of basis vectors (ischemic and non-ischemic) are then derived for each group from the ECG data of the training patients in the group. However, dividing the training populations into groups is not required.

In one embodiment of the invention, the training populations are divided into groups according to locations of ischemic conditions (e.g., anterior, inferior, and other). The selected characteristic used to divide the training populations is the identity of the lead with the greatest ST elevation. For example, in one actual embodiment of the invention, the representative heartbeat for leads I, II, and V3 (i.e., the available leads) are analyzed to determine which lead has the largest ST elevation. If the representative heartbeat for lead I has the largest ST elevation, the patient's ECG is categorized as "other"; if lead II, the patient's ECG is categorized as "inferior"; if lead V3, the patient's ECG is categorized as "anterior."

It is appreciated that alternative groups may be defined according to other selected characteristics. For example, local features other than ST elevation, such as T wave amplitude, QRS area measures, etc., and patient clinical information (e.g., age, sex, etc.), may be used to divide the training populations into groups. Alternatively, selected local features may be classified first to produce a preliminary determination of ischemia that is used as a basis for dividing the training populations. Local features and classification methods suitable for producing preliminary determinations in this regard have been described above in reference to FIGS. 7–11. It is further appreciated that basis vectors may be derived for each of the training populations as a whole, without dividing the training populations into groups.

Figure 13:
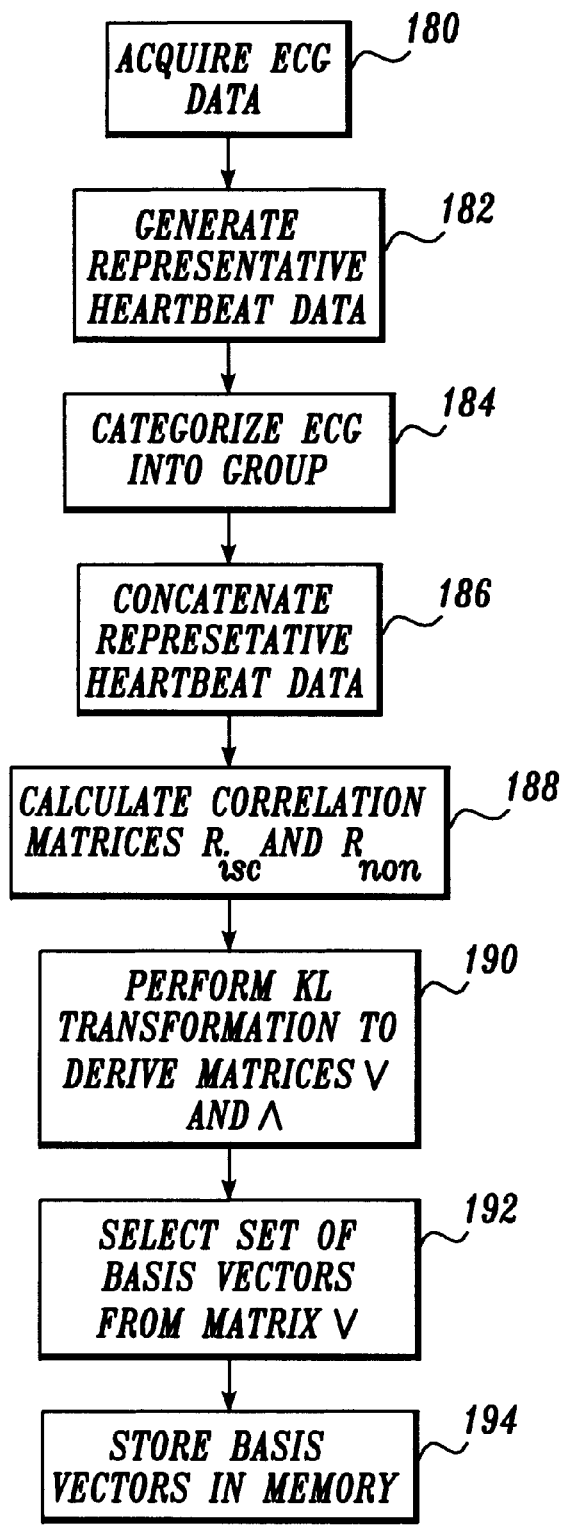
FIG. 13 is a flow diagram illustrating a process performed during a training phase to derive a set of basis rectors used by the acute cardiac ischemia detection process shown in FIG. 12 to detect acute cardiac ischemia.
Figure 15:
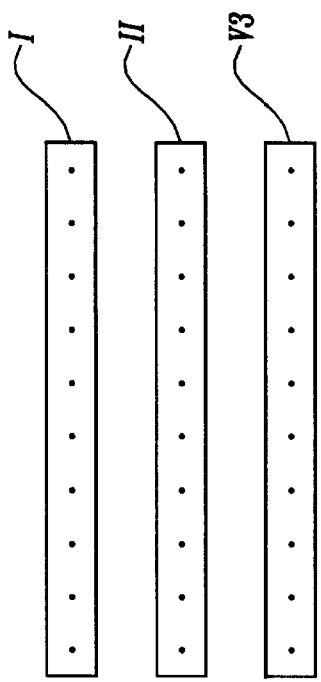
FIG. 15 is a pictorial diagram of three leads of representative heartbeat data generated by the acute cardiac ischemia detection process shown in FIG. 12.

For the sets of ischemic and non-ischemic training patients in each group (or for each training population as a whole if grouping is not performed), a set of basis vectors is derived. FIG. 13 illustrates in more detail a process for deriving basis vectors. In a block 180 in FIG. 13, ECG data is acquired from each of the patients in the ischemic and non-ischemic training populations. The ECG data may be acquired using a conventional 12 lead ECG device or a reduced lead set device 10 such as that shown in FIGS. 2–6 in the manner described earlier in reference to FIG. 8. After acquiring ECG data from each of the training patients, representative heartbeat data is generated in a block 182 from the ECG data in a manner as described earlier in reference to FIG. 9. More specifically, for each patient in the training populations, representative heartbeat data is generated from the ECG data collected on the reduced set of leads (e.g., leads I, II, and V3 ). These leads are depicted generally in FIG. 15 in which dots are used to indicate a series of numbers that, in this regard, forms the representative heartbeat data.

Assuming for the sake of discussion that the training populations are divided into groups according to locations of acute cardiac ischemia, the ECG of each patient in the training populations is categorized into a group in a block 184 according to ST elevation measures calculated for each patient. Next, in a block 186 the representative heartbeat data generated for each patient in each group is concatenated to form a representative heartbeat vector "$\underline{x}$". A concatenated representative heartbeat vector $\underline{x}$ includes, for example, the representative heartbeat data of lead I, immediately followed by lead II and lead III. A concatenated representative heartbeat vector $\underline{x}$ is depicted generally in FIG. 16, with vertical dashed partitions between the lead data shown for illustrative purposes only. It is to be understood that alternative embodiments of the invention may use a different combination of leads than that shown in FIGS. 15 and 16.

Figure 16:
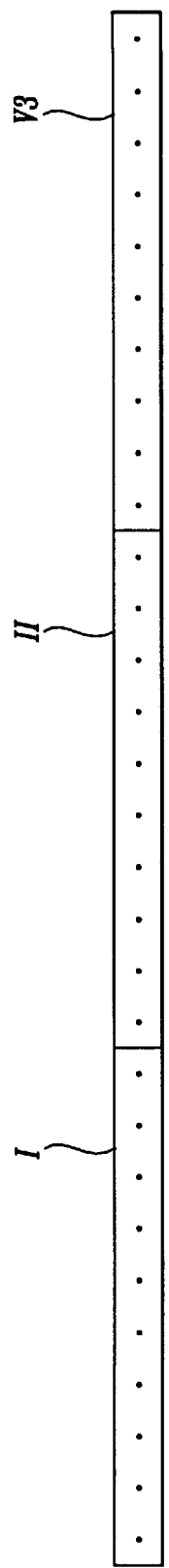
FIG. 16 is a pictorial diagram of a concatenated representative heartbeat vector $\underline{x}$ that includes the representative heartbeat data depicted in FIG. 15.

In an embodiment of the reduced lead set device 10 where three leads of ECG data are acquired at a sampling rate of 500 samples of data per second, and a 480 millisecond segment of data per representative heartbeat is used, each lead (e.g., the leads shown in FIG. 15) includes 240 samples of heartbeat data, thus producing a concatenated representative heartbeat vector $\underline{x}$ (as shown in FIG. 16) having 720 samples of heartbeat data. A concatenated representative heartbeat vector $\underline{x}$ is obtained for each of the patients in the respective training populations.

For each of the ischemic and non-ischemic sets of patients in each group, the patients' concatenated representative heartbeat vectors $\underline{x}$ are combined together in a block 188 in FIG. 13 to calculate correlation matrices $R_{isc}$ and $R_{non}$ using the following general equation:

$$R = \frac{1}{N} \sum_{i=1}^{N} (\underline{x}_i \underline{x}_i^T) \qquad (4)$$

The values in matrix R produced by Equation (4) are normalized according to the total number of patients of patients "N" whose concatenated heartbeat vectors were used. Thus, using Equation (4), a correlation matrix $R_{isc}$ is calculated for the ischemic patients in each group, and a correlation matrix $R_{non}$ is calculated for the non-ischemic patients in each group.

For each correlation matrix R (regardless of whether the training populations are divided into groups), a Karhunen-Loeve (KL) transformation is performed in a block 190 to identify a matrix V and a matrix Λ that satisfy the following general equation:

$$R = V\Lambda V^T \qquad (5)$$

Figure 17A:
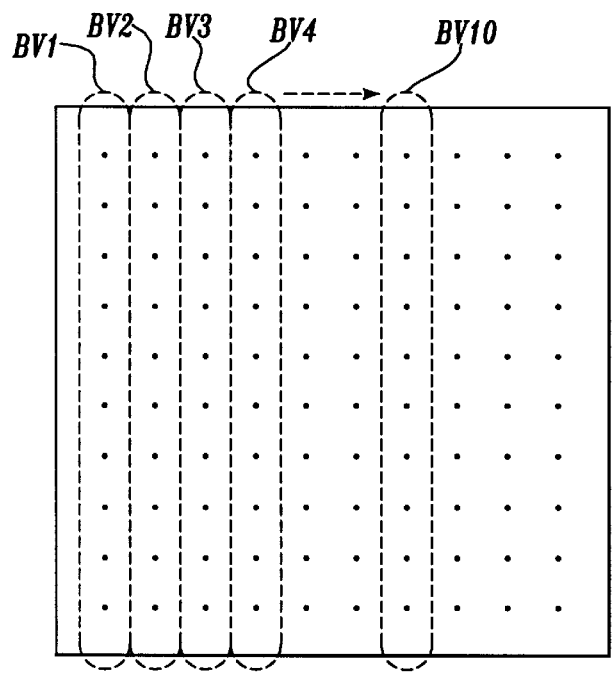
FIGS. 17A and 17B are pictorial diagrams of matrices V and Λ produced during the basis vector derivation process shown in FIG. 13 by performing a Karhunen-Loeve transformation on a correlation matrix R calculated from ECG data obtained from a training population of patients.
Figure 17B:
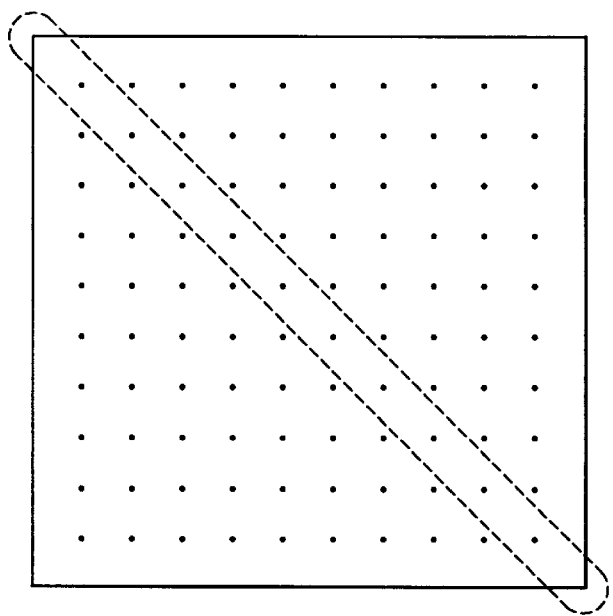

A matrix V and matrix Λ are illustrated generally in FIGS. 17A and 17B, respectively. The columns of the matrix V are mutually orthogonal basis vectors that collectively define the ECG subspace of the concatenated vectors $\underline{x}$ used in Equation (4) to form the correlation matrix R. The matrix Λ in FIG. 17B is a matrix whose diagonal consists of eigenvalues corresponding to the correlation matrix R and are ordered from largest to smallest in value along the diagonal. Likewise, the basis vectors (i.e., the columns in matrix V) are eigenvectors that correspond to the eigenvalues of the correlation matrix R. If the concatenated heartbeat vectors $\underline{x}$ have 720 samples each, then the dimension of both matrix V and matrix Λ, as well as correlation matrix R is 720×720.

Because the eigenvalues in matrix Λ are ordered from largest to smallest value along the diagonal, the initial columns of matrix V which correspond with the eigenvalues of greater value are more significant in terms of signal synthesis than the latter columns of matrix V which correspond with the smaller eigenvalues. In a block 192 of FIG. 13, a set of basis vectors is selected such as the first ten columns of matrix V labeled BF1, BF2, BF3, BF4, . . . , BF10 in FIG. 17A, for later use as preprocessed parameters 67 in computing the current patient's global features. Although subspace representation error theoretically decreases with the inclusion of additional basis vectors, experience thus far has indicated that using more than ten basis vectors does not markedly improve the classification performance in the present invention. Moreover, the basis vectors corresponding to smaller eigenvalues (i.e., the latter columns of matrix V) that are not selected in block 192 are more likely to be affected by noise.

It will be appreciated that other sets of columns, or basis vectors, may be selected from matrix V. For example, instead of selecting the first ten columns of matrix V, a set of basis vectors including the first, third, fifth, and seventh columns may be selected. Basis vectors beyond the first ten columns may also be selected. An optimal set of basis vectors may be determined empirically for the ischemic and non-ischemic training patients in each group.

If the training populations are not divided into groups, a single paired set of basis vectors (i.e., a set of ischemic basis vectors and a set of non-ischemic basis vectors) may be used to represent the ECG subspaces of the ischemic population and the non-ischemic population as a whole. The selected vectors are then stored in a block 194 as preprocessed parameters 67 in memory 64 (FIG. 6) for later use in deriving global features from the ECG of a patient undergoing evaluation.

Returning now to FIG. 12, given a defined number of groups and a paired set of ischemic and non-ischemic basis vectors associated with each group, the ECG of a patient under current evaluation is categorized in a block 164 into the group to which it best pertains according to the lead with the greatest ST elevation as described above for the training populations. Once a patient's ECG is categorized into a particular group, the paired set of basis vectors associated with the group are selected in a block 166 from the preprocessed parameters 67 in memory 64 for use in evaluating the patient's ECG. The patient's representative heartbeat data for each of the available leads is then concatenated in a block 168 to form a concatenated heartbeat vector "$\underline{x}$", in a manner as described earlier for the patients in the training populations. Next, in blocks 170 and 172, the patient's concatenated heartbeat vector $\underline{x}$ is mathematically projected onto the basis vectors selected in block 166. Broadly stated, the projecting operation (described in more detail below) results in a number of projection coefficients that are used as global features of the patient's ECG. The number of global features extracted from the patient's ECG corresponds to the number of basis vectors used in the projecting operation.

Figure 18B:
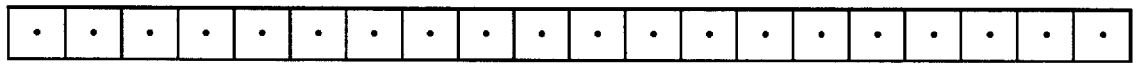
FIG. 18B is a pictorial diagram of a concatenated global feature vector $\underline{f}$ that includes the twenty global features as depicted in FIG. 18A.
Figure 18A:
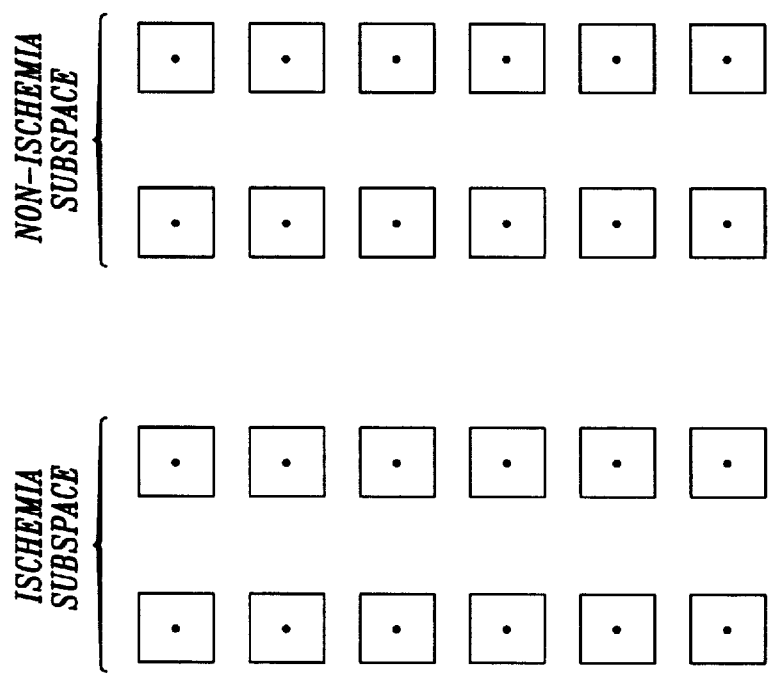
FIG. 18A is a pictorial diagram of twenty projection coefficients ("global features") calculated during the acute cardiac ischemia detection process shown in FIG. 12 by projecting a patient's concatenated representative heartbeat vector $\underline{x}$, as shown in FIG. 16, onto ten basis vectors spanning acute cardiac ischemia ECG subspace and ten basis vectors spanning non-ischemia ECG subspace, the basis vectors being determined beforehand as shown in FIG. 13.

More specifically, the projecting operation involves projecting the patient's concatenated heartbeat vector $\underline{x}$ onto the basis vectors defining an acute cardiac ischemic ECG subspace in block 170 by computing an inner product of the vector $\underline{x}$ with each of the ischemic basis vectors. The patient's concatenated heartbeat vector $\underline{x}$ is also projected onto the basis vectors defining the corresponding non-ischemic ECG subspace in block 172 by computing an inner product of the vector $\underline{x}$ with each of the non-ischemic basis vectors. If, for example, ten basis vectors are used to characterize each of the ischemic and non-ischemic ECG subspaces, the projecting operation results in a total of twenty scalar projection coefficients that are used as global features, as generally depicted in FIG. 18A. Once the patient's concatenated heartbeat vector $\underline{x}$ is projected onto the ischemic and non-ischemic basis vectors in blocks 170 and 172 of FIG. 12 (i.e., once the global features are calculated), the global features are concatenated in a block 174 into a single global feature vector "$\underline{f}$", as generally depicted in FIG. 18B.

Next, in a block 176, the global features derived from the current patient's ECG data are classified to determine whether acute cardiac ischemia is detected. The classifier in block 176 evaluates the global features of the current patient relative to representative global features previously derived during a training phase from patients in the ischemic and non-ischemic training populations. In one actual embodiment of the present invention, a Gaussian classifier is used to compare the current patient's global features with a set of mean global features normalized by covariances previously derived from the training populations. If the current patient's global features are "closer" to the normalized mean global features of the ischemic population than the non-ischemic population (hence, in a graphical sense, define a point "closer" to the ischemic region than the non-ischemic region of the feature space), a report of acute cardiac ischemia is produced.

As with the statistical classifier discussed above in reference to block 110 of FIG. 7, the classifier in block 176 is trained during an earlier training phase. During the training phase (e.g., the training phase in which the ischemic and non-ischemic basis vectors are derived), a vector of mean global features "$\underline{m}$" and a covariance matrix "C" are calculated for each set of ischemic training patients and non-ischemic training patients. In other words, a vector $\underline{M}_{isc}$ and matrix $C_{isc}$, and a vector $\underline{m}_{non}$ and matrix $C_{non}$, are calculated for each group, in the manner described earlier in reference to blocks 154 and 156 of FIG. 11. The vectors of mean global features $\underline{m}_{isc}$ and $\underline{m}_{non}$, and covariance matrices $C_{isc}$ and $C_{non}$, are used in classifying the current patient's global features. The preprocessing performed during the training phase to train the classifier in this regard is shown in more detail in FIG. 14.

Figure 14:
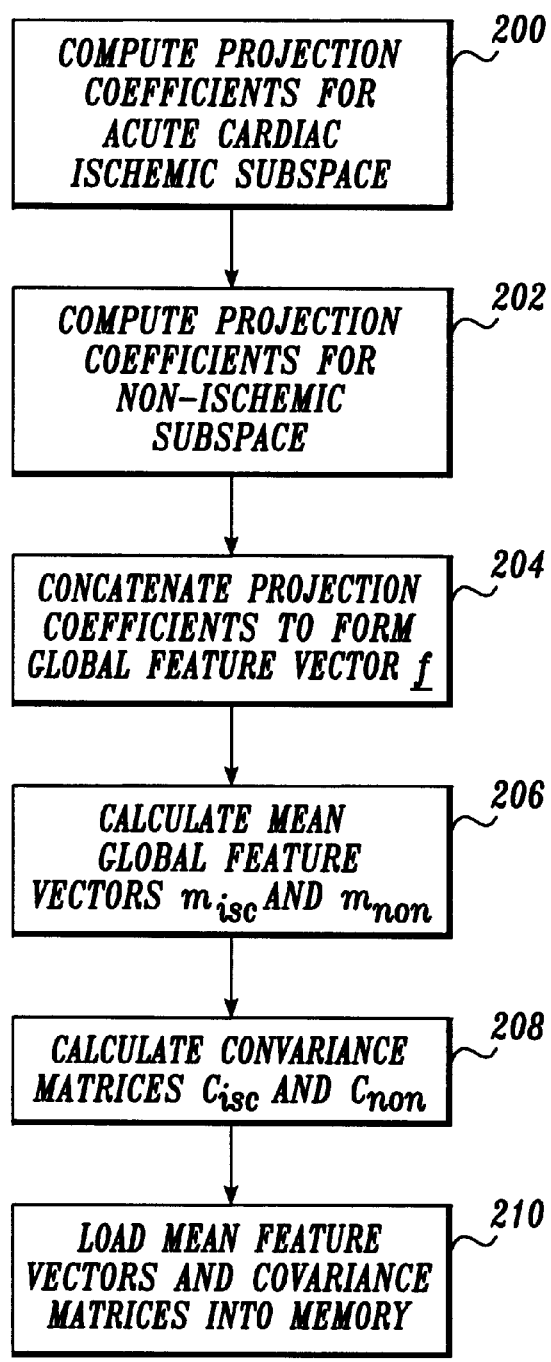
FIG. 14 is a flow diagram illustrating a process performed during the training phase to derive a set of classifier parameters used by the acute cardiac ischemia detection process shown in FIG. 12.

In blocks 200 and 202 of FIG. 14, global features for each patient in each group of training patients are calculated using the basis vectors derived for the group. In that regard, the concatenated representative heartbeat vector $\underline{x}$ produced in block 186 (FIG. 13) for each training patient is mathematically projected onto the ischemic and non-ischemic basis vectors for the training patient's group using an inner product calculation. Next, in a block 204, the resulting ischemic and non-ischemic projection coefficients for each training patient are concatenated to form a global feature vector $\underline{f}$.

Mean feature vectors $\underline{m}_{isc}$ and $\underline{m}_{non}$ are then calculated in a block 206 for each group by computing a feature-by-feature mean of the concatenated global feature vectors $\underline{f}$ produced from the respective ischemic and non-ischemic patients in each group. Covariance matrices $C_{isc}$ and $C_{non}$ are calculated in block 208 for the respective set of ischemic and non-ischemic training patients in each group using Equation (1) above. As noted earlier, the covariance matrix C provides an indication of how widely dispersed the global features of the set of training patients are from the calculated mean global features for the same set of patients. The mean feature vectors $\underline{m}$ and the covariance matrices C are stored in a block 210 as preprocessed parameters 67 in memory 64 (FIG. 6) for later use in classifying the current patient's global features.

Returning to FIG. 12, according to one implementation of the invention, the Gaussian classifier in block 176 evaluates the current patient's global feature vector $\underline{f}$ with respect to the mean global feature vectors $\underline{m}_{isc}$ and $\underline{m}_{non}$, and covariance matrices $C_{isc}$ and $C_{non}$ according to Equation (2) given above. Specifically, the quantity $d_{isc}$ produced by Equation (2) reflects the distance between the patient's global feature vector $\underline{f}$ and the mean global feature vector $\underline{m}_{isc}$ weighted by a covariance matrix $C_{isc}$ for the acute cardiac ischemia ECG subspace. Similarly, the quantity $d_{non}$ reflects the distance between the patient's global feature vector $\underline{f}$ and the mean global feature vector $\underline{m}_{non}$ weighted by the covariance matrix $C_{non}$ for the non-ischemia ECG subspace. The Gaussian classifier in block 176 then compares the quantities $d_{isc}$ and $d_{non}$, and if $d_{isc}$ is less than $d_{non}$, for example, an acute cardiac ischemic condition is detected and reported. More generally stated, if $d_{non}-d_{isc}>t$, where "t" is the decision threshold, acute cardiac ischemia is reported. The sensitivity and specificity of the device 10 may be adjusted by varying the threshold "t", as will be discussed below. Furthermore, while a Gaussian classifier has been described above, it is appreciated that alternative statistical classifiers may be used to evaluate a patient's global features. For descriptions of alternative statistical classifiers suitable for use in the invention, see R. Duda and P. Hart, *Pattern Classification and Scene Analysis* (1973), referenced earlier.

The outcome of the evaluation made by the classifier in block 176 is reported to the user of the device in a block 178. As a further aspect of the invention, if the training populations are divided into groups according to ischemia location, the reported outcome may also identify the location of the ischemic condition (if acute cardiac ischemia is detected) based on the group into which the patient's ECG was categorized. Knowing whether a detected ischemic condition is at an inferior, anterior, or other location may assist a caregiver in treating the ischemic condition.

Although the acute cardiac ischemia detection process 66b described above involves projecting a patient's concatenated heartbeat vector $\underline{x}$ onto basis vectors that collectively define both an acute cardiac ischemic ECG subspace and a non-ischemic ECG subspace, it should be understood that, alternatively, the patient's concatenated heartbeat vector $\underline{x}$ may be projected onto one or more basis vectors that define only an acute cardiac ischemic ECG subspace, i.e., without projection onto any basis vectors that define a non-ischemic ECG subspace. In that regard, only "ischemic" projection coefficients (i.e., ischemic global features) are produced and classified.

A classifier for classifying only ischemic global features does not need to be any different in structure than a classifier that classifies both ischemic and non-ischemic global features, as described above in reference to block 176. The only difference is the number of global features used in the classification and the training of the classifier performed beforehand in a training phase.

In the training phase, the basis vectors defining an acute cardiac ischemic ECG subspace are derived from the ischemic training population as described earlier in reference to FIG. 13. Then, for each training patient in both the ischemic and non-ischemic training populations, ischemic global features are calculated using the derived ischemic basis vectors in the manner described earlier in reference to block 200 in FIG. 14. The ischemic global features for each patient (ischemic and non-ischemic) are concatenated into a global feature vector $\underline{f}$ as described earlier in reference to block 204.

Mean feature vectors $\underline{m}_{isc}$ and $\underline{m}_{non}$ and covariance matrices $C_{isc}$ and $C_{non}$ are then calculated in the manner described in reference to blocks 206 and 208. The vectors $\underline{m}_{isc}$ and $\underline{m}_{non}$, and matrices $C_{isc}$ and $C_{non}$, are stored as preprocessed parameters 67 in the memory 64 for later use in classifying the ischemic global features of the current patient in the manner discussed in reference to block 176.

Alternatively, the patient's concatenated representative heartbeat vector $\underline{x}$ may be projected onto one or more basis vectors that define only a non-ischemic ECG subspace, i.e., without projection onto any basis vectors that define an acute cardiac ischemic ECG subspace. In that regard, only "non-ischemic" projection coefficients (i.e., non-ischemic global features) are produced and classified. The same procedures discussed above for training the classifier are used, except the basis vectors that define a non-ischemic ECG subspace are used instead of the ischemic basis vectors. Furthermore, as discussed earlier, if the training populations are divided into groups according to ischemia location, the reported outcome (if ischemia is detected) also helps identify the location of the ischemic condition.

Acute Cardiac Ischemia Detection Using Local and Global Features

Figure 19:
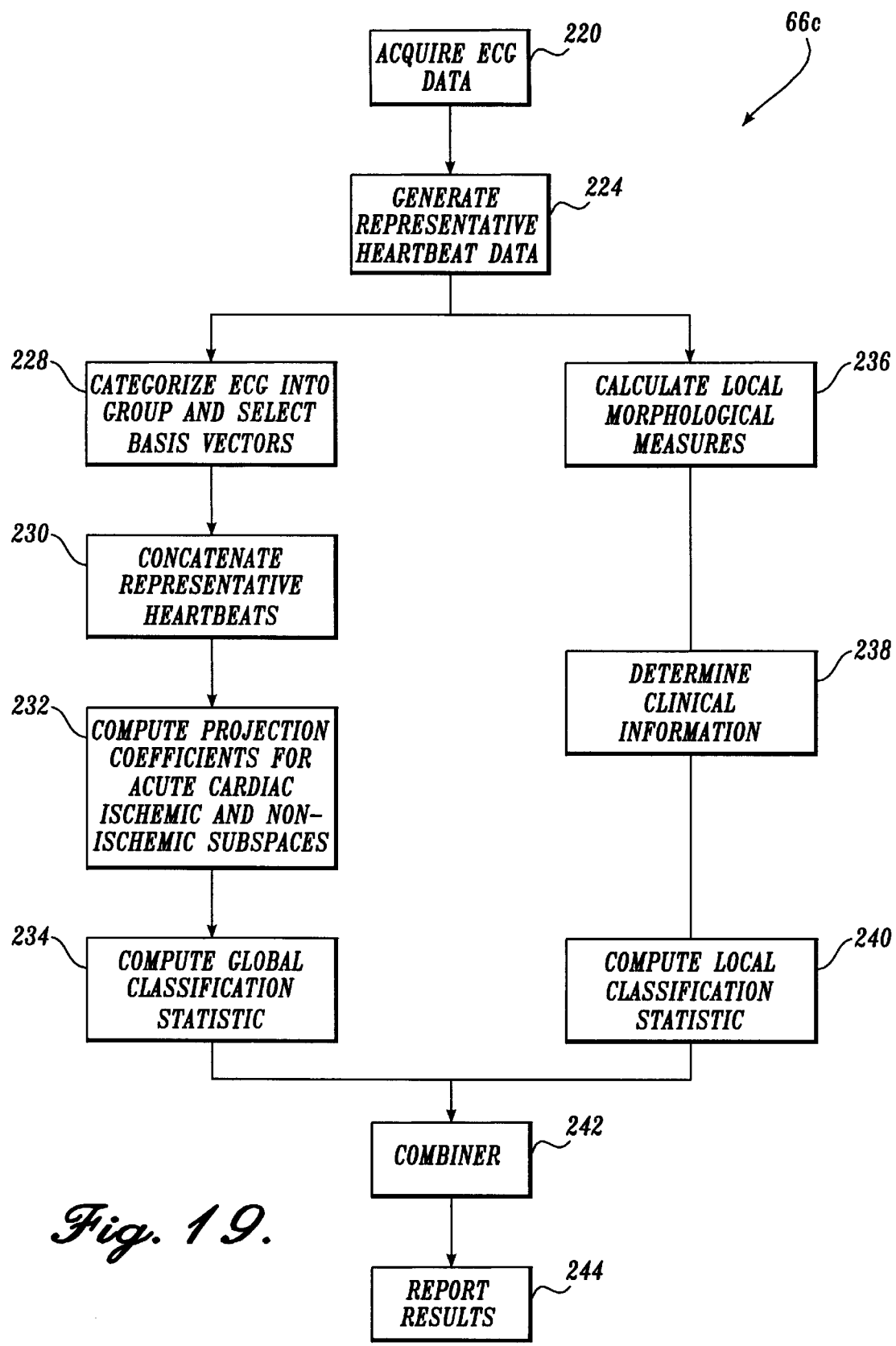
FIG. 19 is a flow diagram illustrating an alternative acute cardiac ischemia detection process conducted by the reduced lead set device shown in FIGS. 2–6 which detects acute cardiac ischemic events by separately classifying local and global features derived from a patient and classifying the results of the separate classifications.

FIG. 19 is a flow diagram that illustrates another version of an acute cardiac ischemia detection process 66c formed in accordance with the present invention. In this version, the reduced lead set device 10 determines and classifies both local features and global features to detect and report the presence of acute cardiac ischemia. In the manner described earlier in reference to FIGS. 7 and 12, the reduced lead set device 10 acquires about ten seconds of ECG data in a block 220 that is amplified and filtered. The reduced lead set device 10 generates in a block 224 representative heartbeat data for each of the available leads in the reduced set of leads. In either a parallel or sequential fashion, the reduced lead set device 10 then calculates both global features in blocks 228, 230, and 232, and local features in blocks 236 and 238.

For local features, selected local morphological measures are calculated in a block 236 from the representative heartbeats generated on the reduced set of leads. Clinical information, such as the age and sex of the patent, may also be obtained in a block 238 for inclusion as local features. The local features are concatenated to form a local feature vector that is input into a local feature classifier in a block 240 that computes a local classification statistic. A suitable classifier in this regard was described earlier in reference to block 110 of FIG. 7. The local classification statistic, however, is not compared with a decision threshold at this time, but instead is provided to a combiner in a block 242.

One or more composite local features may also be calculated and input into the local feature classifier in block 240. Composite local features, in this regard, include a preliminary prediction of acute cardiac ischemia using logistic regression as described above in reference to Equation (3). If the training populations are divided into groups (e.g., anterior, inferior, and other) as described earlier, a logistic regression equation is derived for each of the groups. ECG features of lead I (known to be sensitive to anterior acute cardiac ischemic events) are used in deriving the regression coefficients of an "anterior" logistic regression equation. Likewise, ECG features of leads II and V3 (known to be sensitive to acute cardiac ischemia in an inferior or other location, respectively) are used in deriving an "inferior" and an "other" logistic regression equation. The regression coefficients derived for each of the groups are stored as preprocessed parameters 67 in the memory 64 (FIG. 6) or later use in calculating a probability of detected acute cardiac ischemia in the patient under current evaluation. When evaluating a current patient, a probability of detected acute cardiac ischemia (i.e., a composite local feature) is calculated with respect to each of the groups. Thus, in that regard, an "anterior" composite local feature, and "inferior" composite local feature, and an "other" composite local feature are calculated for the current patient and input into the local feature classifier in block 240.

Another composite feature that may be calculated and input into the local feature classifier in block 240 is a Mahalanobis distance calculated according to Equation (2). In implementations of the invention where ECGs are categorized into groups (e.g., anterior, inferior, and other), a Mahalanobis distance may be calculated for each of the anterior, inferior, and other groups. Using a nearest-neighbor approach, the patient's local features are then identified with a group (either anterior, inferior, other, or non-ischemia) according to the closest calculated distance. This group identification is provided as a composite local feature to the local feature classifier in block 240. Preferably, the local feature classifier receives more than one composite local feature, including one or more composite local features derived by logistic regression and one or more composite local features derived from calculating a Mahalanobis distance. Selected composite local features may also be dichotomized prior to being input into the local feature classifier. The local feature classifier in block 240 produces a local classification statistic that is supplied to a combiner in a block 242 for evaluation in combination with a global classification statistic as discussed below.

For global features, the reduced lead set device 10 categorizes a patient's ECG into a group (i.e., inferior, anterior, or other) in a block 228 and selects the pair of basis vectors belonging to the group. The patient's representative heartbeat data is concatenated in a block 230 into a concatenated heartbeat vector that is projected in a block 232 onto the selected basis vectors. The resulting projection coefficients, or global features, are input into a global feature classifier in a block 234. A suitable classifier in this regard was described earlier in reference to block 176 of FIG. 12. The global classification statistic resulting from the global feature classifier is not compared with a decision threshold at this time but instead is provided to the combiner in block 242.

The combiner in block 242 is a classifier that receives the classification statistics from both the local and global feature classifiers (blocks 240 and 234, respectively). The combiner is preferably a statistical classifier that uses a simple statistical model, such as a linear discriminate classifier or logistic discriminate classifier. The combiner evaluates the local and global classification statistics to produce a combined classification statistic that is compared against a decision threshold "t." If the combined classification statistic exceeds the threshold "t," the local and global classification statistics are classified as belonging to the class of patients experiencing acute cardiac ischemia. On the other hand, if the combined classification statistic is less than a threshold "t," the local and global classification statistics are classified as belonging to the non-ischemic class of patients. The details of constructing suitable classifiers for use in the combiner in block 242 are discussed by R. Duda and P. Hart, *Pattern Classification and Scene Analysis*, referenced earlier. The result of the classification made by the combiner (i.e., whether or not the local features and global features are indicative of acute cardiac ischemia) is reported to the user in a block 244.

Figure 20:
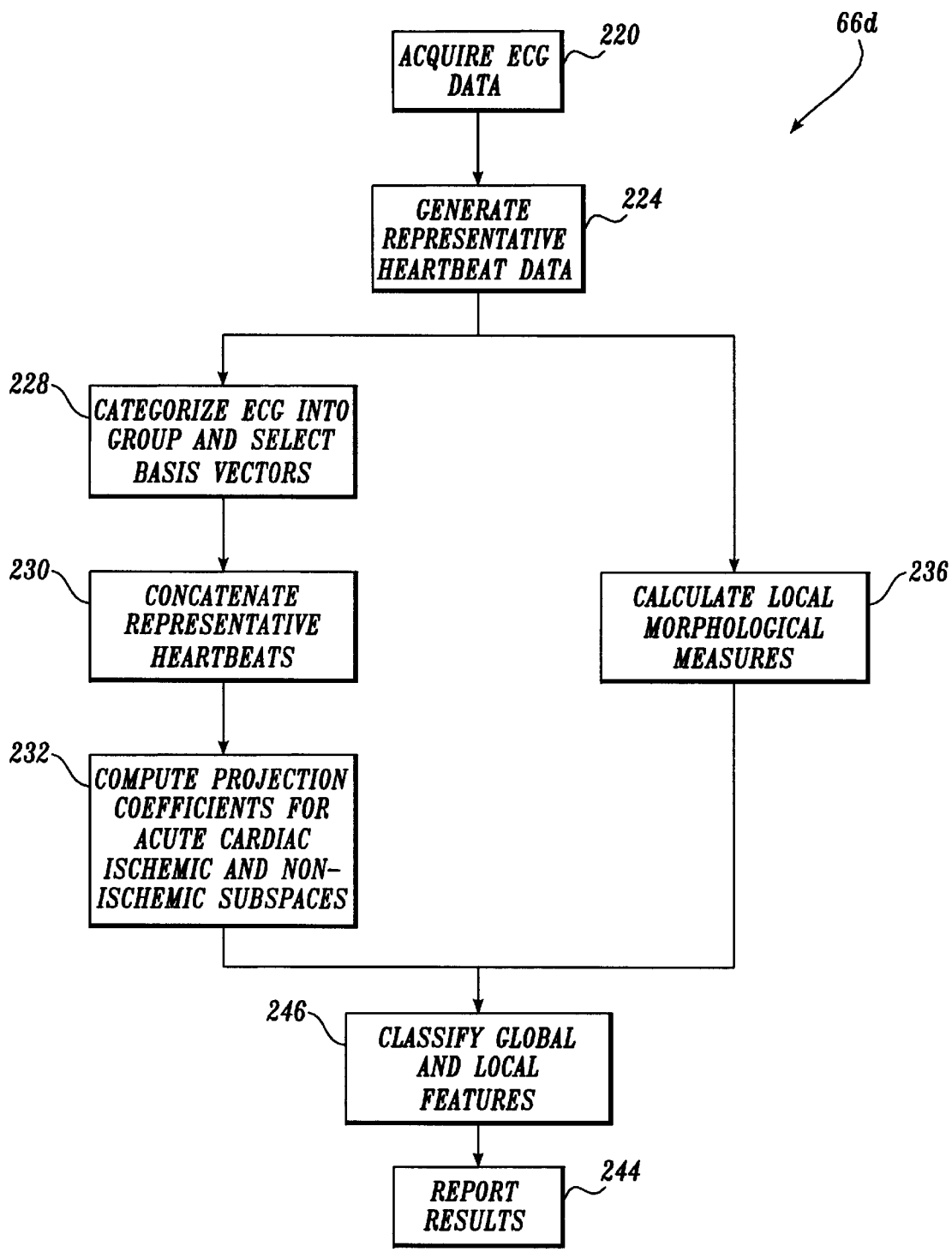
FIG. 20 is a flow diagram illustrating an alternative acute cardiac ischemia detection process conducted by the reduced lead set device shown in FIGS. 2–6 which detects acute cardiac ischemic events by classifying a combination of local and global features.

FIG. 20 illustrates yet another version of an acute cardiac ischemia detection process 66d in which both local and global features are evaluated. In FIG. 20, a single classifier is used in a block 246 in place of the separate local 20 and global feature classifiers (blocks 240 and 232, respectively) and the combiner (block 242) described in reference to FIG. 19. The single classifier in block 246 receives both the global features computed in block 232 and the local features calculated in block 236 as features to be jointly classified. Clinical information, such as the patient's age and sex, may also be input into the classifier in block 246 as additional local features (though not shown in FIG. 20). Alternatively, or in addition to the local features discussed above, composite local features may be calculated and provided to the classifier in block 246 along with the global features.

The classifier in block 246 may be a statistical classifier having a form similar to the classifiers described above. For example, the classifier may be a Gaussian classifier previously trained during a training phase using corresponding sets of local and global features derived from patients in the ischemic and non-ischemic training populations. The current patient's local features and global features are concatenated into a single local/global feature vector. The classifier in block 246 then evaluates the patient's combined local/global feature vector with respect to calculated representative local/global feature vectors derived from the ischemic and non-ischemic populations to produce a local/global classification statistic. The local/global classification statistic is then compared with a decision threshold to determine whether an acute cardiac ischemic condition is present. A logistic regression classifier may be used to evaluate the combined local/global feature set. For additional detail on a logistic regression classifier, see D. Hosmer and S. Lemeshow, *Applied Logistic Regression* (1989), referenced above. Depending on the outcome of the evaluation performed by the classifier in block 246, a report indicating detection of acute cardiac ischemia is produced in block 244.

It should be understood that a classifier is typically implemented as a computer software routine. In reference to FIG. 6, a classifier executed by the processing unit 62 forms part of a computer program that carries out the functions of the acute cardiac ischemia detection process 66. Alternatively, a classifier executed by the processing unit 62 may comprise a separate software routine implemented by a separate processor or circuit in communication with the processing unit 62.

Adjustment of Sensitivity/Specificity

Figure 21:
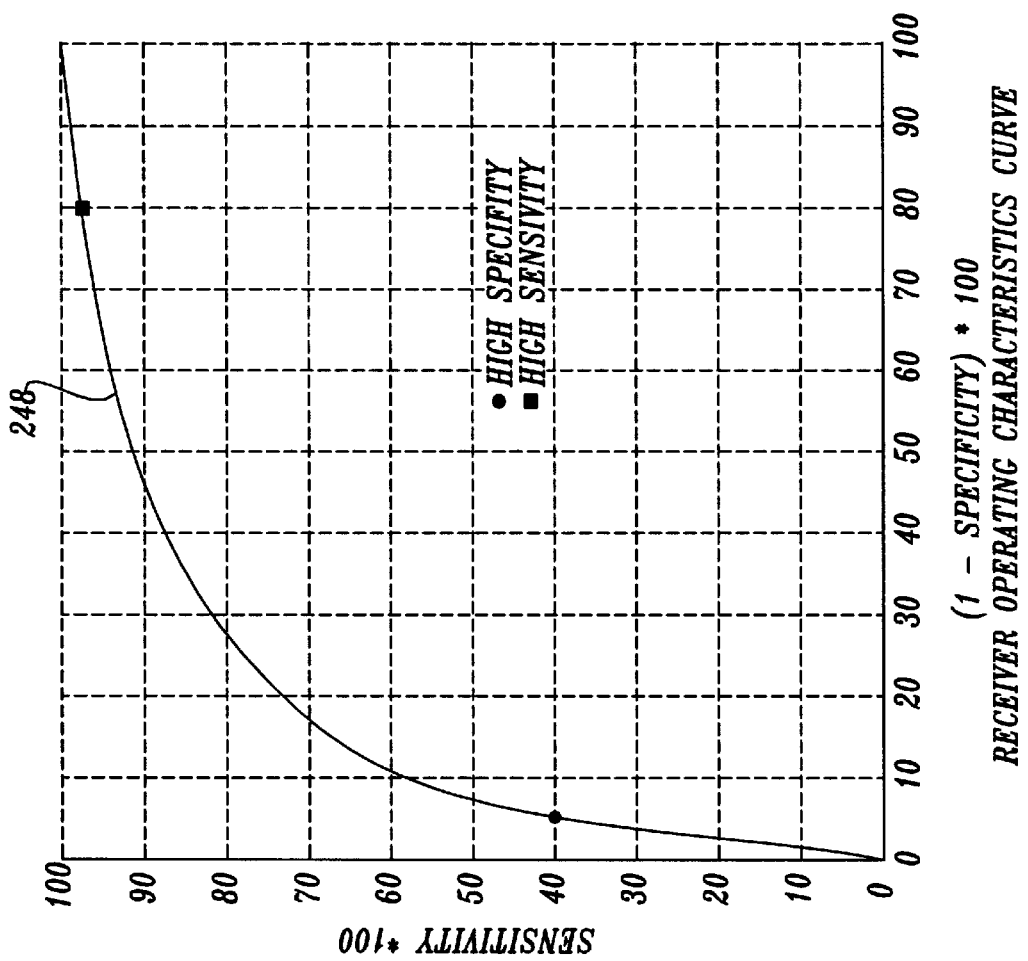
FIG. 21 is a graph of a typical receiver operating characteristics curve depicting sensitivity/specificity tradeoffs which can be implemented by the reduced lead set device shown in FIGS. 2–6.

The ability to identify and correctly determine acute cardiac ischemic events is indicated by the sensitivity and specificity of the reduced lead set device 10. A typical sensitivity/specificity tradeoff is illustrated by a receiver operating characteristics (ROC) curve 248 as shown in FIG. 21. The ordinate in FIG. 21 represents sensitivity, or fraction of true positives detected, and the abscissa represents the quantity of "1-specificity", or fraction of false positives detected. Values on both axes are expressed as percentages. Thus, as shown in FIG. 21, a reduced lead set device 10 tuned to be more sensitive in its analysis is typically less specific, and a reduced lead set device 10 tuned to be more specific is typically less sensitive. If the reduced lead set device 10 could correctly determine all cases, the analysis would have a specificity of one and a sensitivity of one. In the present invention, the point at which a reduced lead set device 10 operates on its ROC curve may be adjusted by varying the decision threshold "t" against which the calculated classification statistic (described earlier) is compared.

In one embodiment of the invention, the classifier threshold, and hence the sensitivity/specificity operating point of the reduced lead set device 10, is set at the time of manufacture in the software that carries out the acute cardiac ischemia detection process 66. Alternatively, the threshold may be adjusted at the point of sale of the reduced lead set device according to the purchaser's needs by adjusting appropriate variables in the software or by setting an internal dial or switch that is read by the software. The reduced lead set device 10 may further be configured to receive a user input (e.g., an external dial, switch, or key input) that selectively adjusts the threshold used by the software, and thus adjusts the sensitivity/specificity operating point of the device. Furthermore, the reduced lead set device 10 may sense the number of electrodes attached to the device and automatically adjust the sensitivity/specificity operating point according to a preset schedule depending on the number of electrodes attached (e.g., operating with higher sensitivity when fewer electrodes are attached).

Figure 23:
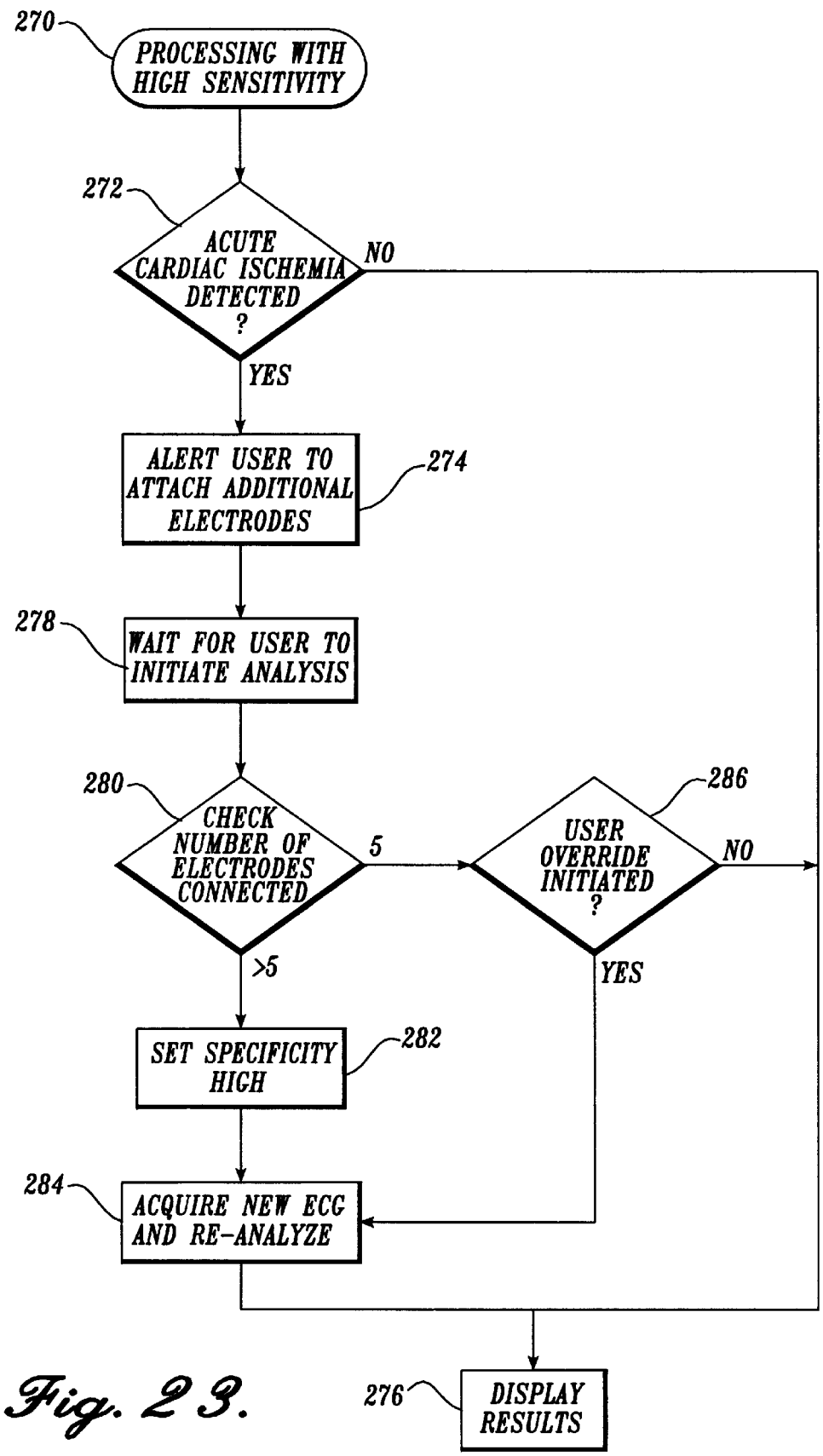
FIG. 23 is a flow diagram illustrating an acute cardiac ischemia detection process conducted by the reduced lead set device shown in FIGS. 2–6 wherein the sensitivity/specificity operating point of the device is adjusted from a high sensitivity to a high specificity operating point in response to additional electrodes being attached to the device.

FIG. 23 is a flow diagram illustrating a procedure for a reduced lead set device 10 to automatically adjust its operating point according to the number of electrodes attached to the device. After initiating an acute cardiac ischemia detection process 66 in a block 250, the reduced lead set device 10 checks its configuration in a block 252 to determine whether it is set to perform the acute cardiac ischemia detection process in a high sensitivity mode or a high specificity mode. If the device is set for a high sensitivity mode, the device then uses leads-off detection circuitry that is well-known in the art to determine the number of electrodes attached to the device in a block 254. If, for example, the reduced lead set device 10 determines that a set of five electrodes is attached, the device adjusts its operating point accordingly in a block 256 to perform the acute cardiac ischemia detection process 66 with high sensitivity. The reduced lead set device 10 adjusts its operating point by adjusting the decision threshold used in the classifier that determines whether acute cardiac ischemia is detected. If the device detects greater than five electrodes, the device adjusts its operating point in a block 258 to perform the acute cardiac ischemia detection process 66 with high specificity.

Figure 22:
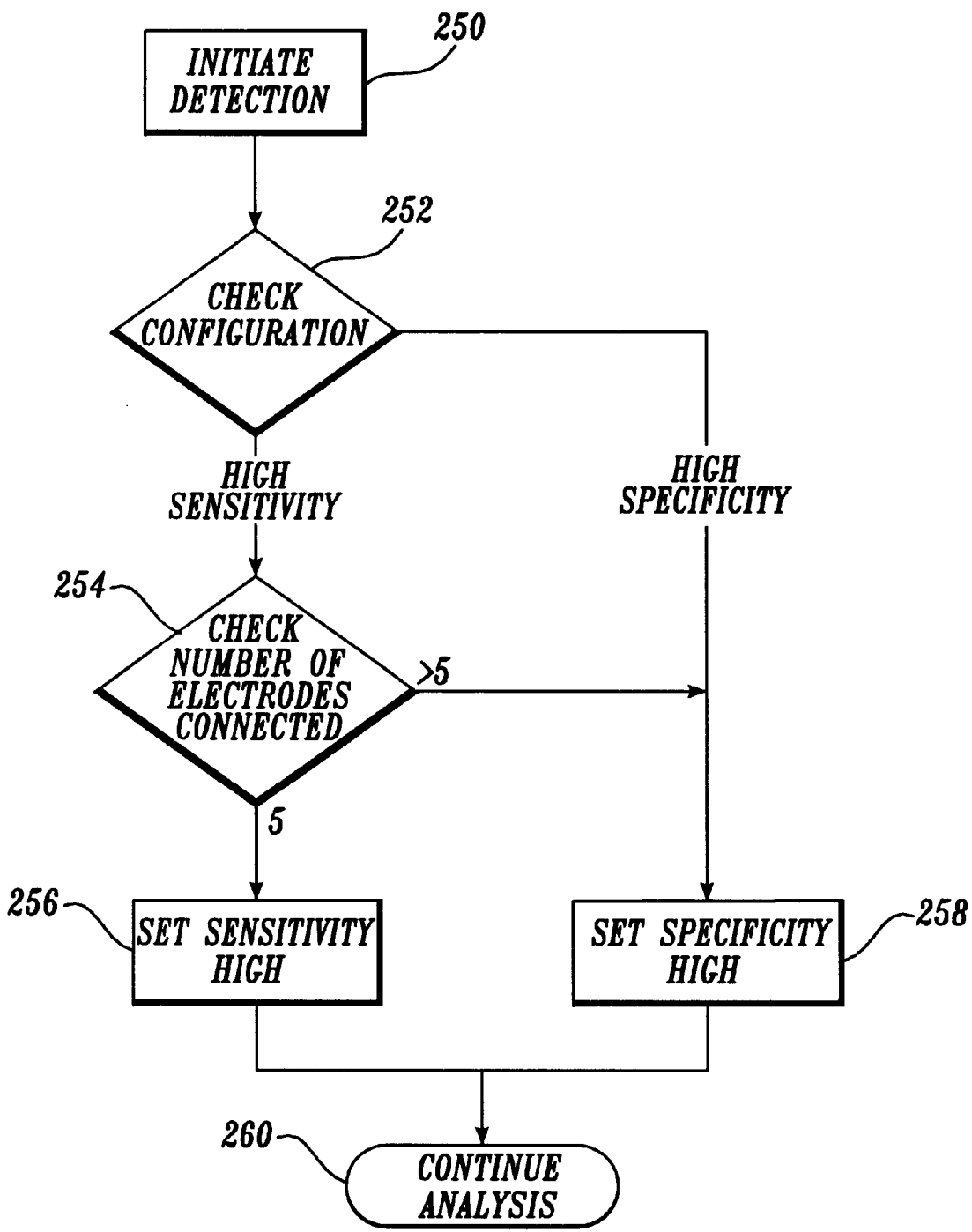
FIG. 22 is a flow diagram illustrating a process for selecting a high sensitivity or high specificity operating point for the reduced lead set device shown in FIGS. 2–6 in performing an acute cardiac ischemia detection process according to the present invention.

Returning to block 252, if the reduced lead set device 10 checks its configuration and finds an initial setting for high specificity, the operating point of the device is adjusted accordingly in block 258. In any event, after adjusting the operating point to a high sensitivity setting in block 256, or to a high specificity setting in block 258, the reduced lead set device 10 proceeds forward with the acute cardiac ischemia detection process in a block 260, including calculating and classifying local features and/or global features, as earlier described. It should be understood that the flow diagram illustrated in FIG. 22 represents only a preliminary part of the acute cardiac ischemia detection process of the present invention.

A further aspect of the present invention is shown in the flow diagram of FIG. 23. In this aspect of the invention, the reduced lead set device 10 adjusts its operating point to a high specificity setting after a user connects additional electrodes to the device. In particular, it is assumed in a block 270 that the acute cardiac ischemia detection process 66 implemented by the reduced lead set device 10 has been performed at least once on the patient and was set for high sensitivity. It is further assumed in FIG. 23 that five electrodes were connected to the reduced lead set device 10 for the ischemia detection process previously performed. The reduced lead set device 10 checks the result of the previous ischemia detection process in a block 272 to see if an acute cardiac ischemic condition was detected. If no such condition was detected, the device continues to display the results of the previous ischemia detection process in a block 276.

On the other hand, if a condition associated with acute cardiac ischemia was detected in the previous ischemia detection process, the reduced lead set device 10 alerts the user in a block 274 to attach additional electrodes and perform the detection process again. In that regard, both visual and audible alerts of a user display may be used. For example, if the electrode configuration of FIG. 3 was used in the previous ischemia detection process, the reduced lead set device 10 may alert the user to connect additional precordial electrodes as shown in FIG. 4. The reduced lead set device 10 waits in a block 278 for the user to attach the additional electrodes and place the electrodes on the patient's skin. The user then reinitiates the detection process by pressing, for example, an ANALYZE button on the device.

In a block 280, the reduced lead set device 10 uses leads-off detection circuitry to determine the number of electrodes connected to the device. If the reduced lead set device detects, for example, only five electrodes, thus indicating that the user did not connect additional leads, the reduced lead set device returns to displaying the results of the previous ischemia detection process in block 276. The device may then return to block 274 and prompt the user again to attach additional electrodes and perform another detection process. In a block 286, the reduced lead set device 10 may also allow the user to initiate a user input to override this procedure and force the reduced lead set device to perform a new ischemia detection process without adding more electrodes.

If the reduced lead set device 10 detects additional electrodes in block 280, the device adjusts its operating point in a block 282 to a high specificity. The device subsequently acquires new ECG data and performs the acute cardiac ischemia detection process in a block 284 by calculating and classifying local features and/or global features, as previously described. With an increased number of electrodes, the reduced lead set device 10 may select and evaluate ECG data on a greater number of leads. A suitable ischemia detection process using a full 12-lead configuration is described in greater detail in copending application Ser. No. 09/209,879, entitled "Method and Apparatus for Detecting a Condition Associated with Acute Cardiac Ischemia," which is incorporated herein by reference. The result of the repeated ischemia detection process is displayed in a block 276. It is anticipated that repeating the ischemia detection process with additional electrodes in a high specificity mode will confirm whether a previous detection of acute cardiac ischemic condition was accurate. In this fashion, the reduced lead set device 10 may be used for making treatment decisions as well as for screening patients for acute cardiac ischemia.

While various embodiments of the invention have been illustrated and described herein, it is appreciated that changes may be made without departing from the spirit and scope of the invention. For example, rather than concatenating the representative heartbeat data on each of the reduced set of leads and projecting the concatenated heartbeat vector onto the basis vectors, each of the particular leads may be individually projected onto a set of basis vectors derived for the particular lead, with the resulting projection coefficients being used as global features. It should also be understood that with sufficient human expert evaluation of global features, classifying a set of global features may be performed heuristically. Furthermore, when reporting whether an acute cardiac ischemic condition is detected, a reduced lead set device 10 constructed according to the invention may report a range of probability of acute cardiac ischemia (e.g., the likelihood of acute cardiac ischemia on a scale of 1–10) instead of reporting a binary "yes/no" result. In that regard, rather than comparing a classification statistic to a single decision threshold (to produce a binary result), the classification statistic may be quantized into a range of values, with the closest value in the range of values being reported to the user. Given the foregoing, it is intended, therefore, that the scope of the invention be determined from the claims that follow and equivalents thereto.

The embodiments of the invention in which an exclusive property or privilege is claimed are defined as follows:

1. A reduced lead set device for detecting and reporting a condition associated with acute cardiac ischemia in a patient, comprising:

(a) a reduced set of electrodes for sensing ECG signals of the patient, wherein the reduced set of electrodes includes less than ten electrodes;

(b) a processing unit in communication with the reduced set of electrodes, the processing unit configured to:
   (i) derive a reduced set of lead data from the ECG signals;
   (ii) calculate features from the reduced set of lead data; and
   (iii) classify the features to determine whether the patient has an acute care ischemic or non-ischemic condition; and (c) a user output in communication with the processing unit for directly reporting to a user of the reduced lead set device whether the patient's cardiac condition was determined ischemic.

2. The reduced lead set device of claim 1, wherein the reduced set of electrodes includes defibrillator electrodes.

3. The reduced lead set of device of claim 1, wherein the reduced set of electrodes includes four limb electrodes and a precordial electrode.

4. The reduced lead set device of claim 1, wherein the processing unit is configured to:

(a) calculate measures of local morphological features in the reduced set of lead data to produce a set of local features; and (b) include the set of local features in the features classified by the processing unit.

5. A reduced lead set device for detecting and reporting a condition associated with acute cardiac ischemia in a patient, comprising:

(a) a reduced set of electrodes for sensing ECG signals of the patient, wherein the reduced set of electrodes includes less than ten electrodes;

(b) a processing unit in communication with the reduced set of electrodes, the processing unit configured to:
   (i) derive a reduced set of lead data from the ECG signals;
   (ii) form a vector of heartbeat data from the reduced set of lead data;
   (iii) produce a set of global features by projecting the vector of heartbeat data onto one or more predetermined basis vectors that define an acute cardiac ischemic ECG subspace or a non-ischemic ECG subspace; and
   (iv) classify the global features to determine whether the features are indicative of an acute cardiac ischemic condition; and (c) a user output in communication with the processing unit for reporting whether the acute cardiac ischemic condition is determined to be present.

6. The reduced lead set device of claim 5, wherein the processing unit is configured to classify the global features to produce a first classification statistic, and wherein the processing unit is further configured to:

(a) obtain a set of local features from the patient;

(b) classify the local features to produce a second classification statistic, and (c) classify the first and second classification statistics to determine whether the first and second classification statistics are indicative of the acute cardiac ischemic condition.

7. The reduced lead set device of claim 5, wherein the processing unit is further configured to obtain a set of local features from the patient and jointly classify the global features and the local features to determine whether the acute cardiac ischemic condition present.

8. A reduced lead set device for detecting and reporting a condition associated with acute cardiac ischemia in a patient, comprising:
(a) a reduced set of electrodes for sensing ECG signals of the patient, wherein the reduced set of electrodes includes less than ten electrodes;
(b) a processing unit in communication with the reduced set of electrodes, the processing unit configured to:
 (i) derive a reduced set of lead data from the ECG signals;
 (ii) calculate features from the reduced set of lead data;
 (iii) generate a classification statistic from the features; and
 (iv) compare the classification statistic with a predetermined threshold to determine whether the features are indicative of an acute cardiac ischemic condition, the threshold reflecting a desired sensitivity/specificity operating point of the reduced lead set device; and
(c) a user output in communication with the processing unit for reporting whether the acute cardiac ischemic condition is determined to be present.

9. The reduced lead set device of claim 8, further comprising an input device in communication with the processing unit for permitting a user of the reduced lead set device to select the sensitivity/specificity operating point.

10. The reduced lead set device of claim 8, wherein the processing unit is further configured to automatically adjust the sensitivity/specificity operating point in accordance with the number of electrodes in the reduced set of electrodes.

11. The reduced lead set device of claim 8, further comprising additional electrodes for sensing ECG signals, wherein the processing unit is configured to:
(a) advise a user of the reduced lead set device to attach the additional electrodes to the reduced lead device; and
(b) obtain and classify additional ECG data using the additional electrodes if the acute cardiac ischemic condition is determined to be present.

12. The reduced lead set device of claim 11, wherein the processing unit is further configured to detect attachment of the additional electrodes to the reduced lead set device and automatically adjust the sensitivity/specificity operating point to a higher level of specificity when the additional electrodes are attached to the reduced lead set device.

13. A method of using a reduced set of lead data to detect and report a condition associated with acute cardiac ischemia in a patient, comprising:
(a) sensing ECG signals of the patient using a reduced set of electrodes placed on the patient, wherein the reduced set of electrodes includes less than ten electrodes;
(b) generating the reduced set of lead data from the sensed ECG signals;
(c) deriving a local morphological measure from the reduced set of lead data;
(d) deriving a set of local features from the patient and including the local morphological measure in the set of local features;
(e) classifying the set of local features to determine whether the patient has an acute cardiac ischemic or non-ischemic condition; and
(f) directly reporting whether the patient's cardiac condition was determined ischemic.

14. The method of claim 13, further comprising:
(a) concatenating the set of local features to form a local feature vector;
(b) evaluating the local feature vector relative to a predetermined local feature vector representative of a training population to produce a classification statistic; and
(c) comparing the classification statistic with a threshold to determine whether the patient has an acute cardiac ischemic condition.

15. The method of claim 14, further comprising selecting the threshold in accordance with a desired sensitivity/specificity tradeoff.

16. The method of claim 13, wherein classifying the set of local features includes applying heuristic rules to the set of local features.

17. A method of using a reduced set of lead data to detect and report a condition associated with acute cardiac ischemia in a patient, comprising:
(a) sensing ECG signals of the patient using a reduced set of electrodes placed on the patient, wherein the reduced set of electrodes includes less than ten electrodes;
(b) generating the reduced set of lead data from the sensed ECG signals;
(c) forming a vector of heartbeat data from the reduced set of lead data;
(d) producing a set of global features by projecting the vector of heartbeat data onto one or more basis vectors that define an acute cardiac ischemic ECG subspace or a non-ischemic ECG subspace;
(e) classifying the set of global features to determine whether the global features are indicative of an acute cardiac ischemic condition; and
(f) reporting whether the acute cardiac ischemic condition is determined to be present.

18. The method of claim 17, wherein forming the vector of heartbeat data includes:
(a) analyzing the reduced set of lead data to identify one or more heartbeats;
(b) generating representative heartbeat data for each lead in the reduced set of lead data; and
(c) concatenating the representative heartbeat data for each lead in the reduced set of lead data to form the vector of heartbeat data.

19. The method of claim 17, wherein producing the set of global features includes:
(a) calculating an inner product of the vector of heartbeat data and one or more basis vectors that define the acute cardiac ischemic ECG subspace to produce a corresponding number of ischemic condition projection coefficients;
(b) calculating an inner product of the vector of heartbeat data and one or more basis vectors that define the non-ischemic ECG subspace to produce a corresponding number of non-ischemic condition projection coefficients; and
(c) using the ischemic condition projection coefficients and the non-ischemic condition projection coefficients as the set of global features.

20. The method of claim 17, further comprising:
(a) defining a plurality of groups wherein each group has basis vectors associated therewith that define the acute cardiac ischemic ECG subspace and the non-ischemic ECG subspace;

(b) categorizing the reduced set of lead data into a group in the plurality of groups; and (c) using the basis vectors of the group into which the reduced set of lead data is categorized as the basis vectors onto which the vector of heartbeat data is projected.

21. The method of claim 20, wherein categorizing the reduced set of lead data into a group includes:

(a) defining each group of the plurality of groups to correspond to a location of an acute cardiac ischemic condition;

(b) deriving from the patient one or more local features;

(c) selecting a local feature derived from the patient;

(d) categorizing the reduced set of lead data into a group based on the selected local feature; and (e) if the acute cardiac ischemic condition is determined to be present, then reporting the location of the acute cardiac ischemic condition corresponding to the group into which the reduced set of lead data is categorized.

22. The method of claim 21, wherein the local feature is an ST elevation measured on a lead in the reduced set of leads, and wherein the reduced set of lead data is categorized into a group according to the lead with the greatest ST elevation.

23. The method of claim 17, wherein classifying the set of global features includes:

(a) concatenating the set of global features to form a global feature vector;

(b) producing a classification statistic by evaluating the global feature vector relative to a predetermined global feature vector representative of a training population; and (c) comparing the classification statistic with a threshold to determine whether an acute cardiac ischemic condition is detected.

24. The method of claim 23, further comprising selecting the threshold in accordance with a desired sensitivity/specificity tradeoff.

25. A method of using a reduced set of lead data to detect and report a condition associated with acute cardiac ischemia in a patient, comprising:

(a) sensing ECG signals of the patient using a reduced set of electrodes placed on the patient, wherein the reduced set of electrodes includes less than ten electrodes;

(b) generating the reduced set of lead data from the sensed ECG signals;

(c) forming a vector of heartbeat data from the reduced set of lead data;

(d) generating a local classification statistic by
  (i) deriving a set of local features from the patient; and
  (ii) classifying the set of local features to produce the local classification statistic;

(e) generating a global classification statistic by
  (i) producing a set of global features by projecting the vector of heartbeat data onto one or more basis vectors that define an acute cardiac ischemic ECG subspace or a non-ischemic ECG subspace; and
  (ii) classifying the set of global features to produce the global classification statistic;

(f) classifying the local classification statistic and the global classification statistic to determine whether the local and global classification statistics are indicative of an acute cardiac ischemic condition; and (g) reporting whether the acute cardiac ischemic condition is determined to be present.

26. The method of claim 25, wherein forming the vector of heartbeat data includes:

(a) analyzing the reduced set of lead data to identify one or more heartbeats;

(b) generating representative heartbeat data for each lead in the reduced set of lead data; and (c) concatenating the representative heartbeat data for each lead in the reduced set of lead data to form the vector of heartbeat data.

27. The method of claim 25, wherein classifying the set of local features includes:

(a) concatenating the set of local features to form a local feature vector; and (b) evaluating the local feature vector relative to a predetermined local feature vector representative of a training population to produce the local classification statistic.

28. The method of claim 25, wherein classifying the set of local features includes:

(a) producing a composite local feature from calculating a probability of detection by applying one or more local features in the set of local features to a logistic regression equation; and (b) classifying the composite local feature in producing the local classification statistic.

29. The method of claim 25, wherein classifying the set of local features includes:

(a) concatenating the set of local features to form a local feature vector;

(b) producing a composite local feature from calculating a Mahalanobis distance between the local feature vector and a predetermined local feature vector representative of a training population; and (c) classifying the composite local feature in producing the local classification statistic.

30. The method of claim 25, wherein producing the set of global features includes:

(a) calculating an inner product of the vector of heartbeat data and one or more basis vectors that define the acute cardiac ischemic ECG subspace to produce a corresponding number of ischemic condition projection coefficients;

(b) calculating an inner product of the vector of heartbeat data and one or more basis vectors that define the non-ischemic ECG subspace to produce a corresponding number of non-ischemic condition projection coefficients; and (c) using the ischemic condition projection coefficients and the non-ischemic condition projection coefficients as the set of global features.

31. The method of claim 25, further comprising:

(a) defining a plurality of groups wherein each group has basis vectors associated therewith that define the acute cardiac ischemic ECG subspace and the non-ischemic ECC subspace;

(b) categorizing the reduced set of lead data into a group in the plurality of groups; and (c) using the basis vectors of the group into which the reduced set of lead data is categorized as the basis vectors onto which the vector of heartbeat data is projected.

32. The method of claim 31, wherein categorizing the reduced set of lead data into a group includes:

(a) defining each group of the plurality of groups to correspond to a location of an acute cardiac ischemic condition;

(b) deriving from the patient one or more local features;

(c) selecting a local feature derived from the patient;

(d) categorizing the reduced set of lead data into a group based on the selected local feature; and (e) if the acute cardiac ischemic condition is determined to be present, then reporting the location of the acute cardiac ischemic condition corresponding to the group into which the reduced set of lead data is categorized.

33. The method of claim 32, wherein the local feature is an ST elevation measured on a lead in the reduced set of leads, and wherein the reduced set of lead data is categorized into a group according to the lead with the greatest ST elevation.

34. The method of claim 25, wherein classifying the set of global features includes:

(a) concatenating the set of global features to form a global feature vector; and (b) evaluating the global feature vector relative to a predetermined global feature vector representative of a training population to produce the global classification statistic.

35. The method of claim 25, wherein classifying the local and global classification statistics includes:

(a) producing a combined classification statistic by evaluating the local and global classification statistics relative to corresponding predetermined local and global classification statistics representative of a training population; and (b) comparing the combined classification statistic with a threshold to determine whether an acute cardiac ischemic condition is detected.

36. The method of claim 35, further comprising selecting the threshold in accordance with a desired sensitivity/specificity tradeoff.

37. A method of using a reduced set of lead data to detect and report a condition associated with acute cardiac ischemia in a patient, comprising:

(a) sensing ECG signals of the patient using a reduced set of electrodes placed on the patient, wherein the reduced set of electrodes includes less than ten electrodes;

(b) generating the reduced set of lead data from the sensed ECG signals;

(c) forming a vector of heartbeat data from the reduced set of lead data;

(d) producing a set of global features by projecting the vector of heartbeat data onto one or more basis vectors that define an acute cardiac ischemic ECG subspace or a non-ischemic ECG subspace;

(e) deriving a set of local features from the patient;

(f) jointly classifying the set of global features and the set of local features to determine whether the global features and local features are indicative of an acute cardiac ischemic condition; and (g) reporting whether the acute cardiac ischemic condition is determined to be present.

38. The method of claim 37, wherein forming the vector of heartbeat data includes:

(a) analyzing the reduced set of lead data to identify one or more heartbeats;

(b) generating representative heartbeat data for each lead in the reduced set of lead data; and (c) concatenating the representative heartbeat data for each lead in the reduced set of lead data to form the vector of heartbeat data.

39. The method of claim 37, wherein the set of local features jointly classified with the set of global features includes a composite local feature based on a probability of detection calculated by applying one or more local features in the set of local features to a logistic regression equation.

40. The method of claim 37, wherein the set of local features jointly classified with the set of global features includes a composite local feature calculated by (a) concatenating the set of local features to form a local feature vector; and (b) calculating a Mahalanobis distance between the local feature vector and a predetermined local feature vector representative of a training population.

41. The method of claim 37, wherein producing the set of global features includes:

(a) calculating an inner product of the vector of heartbeat data and one or more basis vectors that define the acute cardiac ischemic ECG subspace to produce a corresponding number of ischemic condition projection coefficients;

(b) calculating an inner product of the vector of heartbeat data and one or more basis vectors that define the non-ischemic ECG subspace to produce a corresponding number of non-ischemic condition projection coefficients; and (c) using the ischemic condition projection coefficients and the non-ischemic condition projection coefficients as the set of global features.

42. The method of claim 37, further comprising:

(a) defining a plurality of groups wherein each group has basis vectors associated therewith that define the acute cardiac ischemic ECG subspace and the non-ischemic ECG subspace;

(b) categorizing the reduced set of lead data into a group in the plurality of groups; and (c) using the basis vectors of the group into which the reduced set of lead data is categorized as the basis vectors onto which the vector of heartbeat data is projected.

43. The method of claim 42, wherein categorizing the reduced set of lead data into a group includes:

(a) defining each group of the plurality of groups to correspond to a location of an acute cardiac ischemic condition;

(b) deriving from the patient one or more local features;

(c) selecting a local feature derived from the patient;

(d) categorizing the reduced set of lead data into a group based on the selected local feature; and (e) if the acute cardiac ischemic condition is determined to be present, then reporting the location of the acute cardiac ischemic condition corresponding to the group into which the reduced set of lead data is categorized.

44. The method of claim 43, wherein the local feature is an ST elevation measured on a lead in the reduced set of leads, and wherein the reduced set of lead data is categorized into a group according to the lead with the greatest ST elevation.

45. The method of claim 37, wherein jointly classifying the set of global features and the set of local features includes:

(a) concatenating the set of local features and the set of global features to form a global/local feature vector; and (b) producing a global/local classification statistic by evaluating the global/local feature vector relative to a predetermined global/local feature vector representative of a training population; and (c) comparing the global/local classification statistic with a threshold to determine whether an acute cardiac ischemic event is detected.

46. The method of claim 45, further comprising selecting the threshold in accordance with a desired sensitivity/specificity tradeoff.

47. A method of using a reduced set of lead data to detect and report a condition associated with acute cardiac ischemia in a patient, comprising:

(a) sensing ECG signals of the patient using a reduced set of electrodes placed on the patient, wherein the reduced set of electrodes includes less than ten electrodes;

(b) generating the reduced set of lead data from the sensed ECG signals (c) deriving at least one characteristic from the reduced set of lead data that is reflective of cardiac condition;

(d) calculating a classification statistic based on the derived characteristic;

(e) comparing the classification statistic with a threshold to determine whether an acute cardiac ischemic condition is detected, wherein the threshold is selected in accordance with a desired sensitivity/specificity operating point; and (f) reporting whether the acute cardiac ischemic condition is determined to be present.

48. The method of claim 47, further comprising adjusting the sensitivity/specificity operating point in response to an instruction by a user, wherein the sensitivity/specificity operating point is adjusted by adjusting the threshold with which the classification statistic is compared.

49. The method of claim 48, further comprising:

(a) determining the number of electrodes in the reduced set of electrodes; and (b) adjusting the sensitivity/specificity operating point based on the number of electrodes in the reduced set of electrodes.

50. The method of claim 47, further comprising advising a user to increase the number of electrodes in the reduced set of electrodes in response to a detected acute cardiac ischemic condition and after the number of electrodes in the reduced set of electrodes is increased, repeating steps (a)–(f) to confirm whether acute cardiac ischemia is determined to be present.

51. The method of claim 50, further comprising adjusting the sensitivity/specificity operating point to a higher level of specificity prior to repeating steps (a)–(f).

52. The method of claim 50, wherein if the number of electrodes in the reduced set of electrodes is not increased but a user override has been initiated, then repeating steps (a)–(f).

* * * * *

UNITED STATES PATENT AND TRADEMARK OFFICE
CERTIFICATE OF CORRECTION

PATENT NO. : 6,217,525 B1
DATED : April 17, 2001
INVENTOR(S) : D.K. Medema et al.

It is certified that error appears in the above-identified patent and that said Letters Patent is hereby corrected as shown below:

Column 28,
Line 19, "set of device" should read -- set device --.
Line 60, "statistic, and" should read -- statistic; and --

Column 29,
Line 2, "condition present." should read -- condition is present. --

Column 34,
Line 65, delete "and"

Column 35,
Line 17, "ECG signals" should read -- ECG signals; --

Column 36,
Line 16, "condition and" should read -- condition, and --

Signed and Sealed this

Twenty-ninth Day of January, 2002

Attest:

Attesting Officer

JAMES E. ROGAN
Director of the United States Patent and Trademark Office